US010695736B2

(12) United States Patent
Yang et al.

(10) Patent No.: US 10,695,736 B2
(45) Date of Patent: Jun. 30, 2020

(54) ARRAY INDUCED ELECTRIC FIELD FLUID REACTION SYSTEM AND APPLICATIONS THEREOF

(71) Applicant: Jiangnan University, Wuxi (CN)

(72) Inventors: Na Yang, Wuxi (CN); Xueming Xu, Wuxi (CN); Yamei Jin, Wuxi (CN); Zhengjun Xie, Wuxi (CN); Zhengyu Jin, Wuxi (CN)

(73) Assignee: JIANGNAN UNIVERSITY, Jiangsu Province (CN)

( * ) Notice: Subject to any disclaimer, the term of this patent is extended or adjusted under 35 U.S.C. 154(b) by 373 days.

(21) Appl. No.: 15/559,662

(22) PCT Filed: Jul. 20, 2016

(86) PCT No.: PCT/CN2016/090710
§ 371 (c)(1),
(2) Date: Sep. 19, 2017

(87) PCT Pub. No.: WO2018/006444
PCT Pub. Date: Jan. 11, 2018

(65) Prior Publication Data
US 2019/0118153 A1    Apr. 25, 2019

(30) Foreign Application Priority Data
Jul. 6, 2016 (CN) .......................... 2016 1 0530097

(51) Int. Cl.
*B01J 19/00* (2006.01)
*H04B 5/00* (2006.01)
(Continued)

(52) U.S. Cl.
CPC ............. *B01J 19/0046* (2013.01); *A23F 3/16* (2013.01); *A23J 3/00* (2013.01); *A23J 3/04* (2013.01);
(Continued)

(58) Field of Classification Search
CPC .................. B01J 19/0046; B01J 19/087; B01J 2219/00495; B01J 2219/00418;
(Continued)

(56) References Cited

U.S. PATENT DOCUMENTS

| 2011/0121834 A1* | 5/2011 | Soutome | G01R 33/365 324/318 |
| 2014/0111475 A1* | 4/2014 | Bae | G06F 3/041 345/174 |

FOREIGN PATENT DOCUMENTS

| CN | 104826569 A | * | 8/2015 | |
| CN | 105304298 A | * | 2/2016 | ............. H01F 38/14 |

* cited by examiner

*Primary Examiner* — Quang T Van
(74) *Attorney, Agent, or Firm* — PROI Intellectual Property US; Klaus Michael Schmid

(57) ABSTRACT

The array induced electric field fluid reaction system includes a reaction unit array with a plurality of reaction units interactively connected as a network configuration, a power supply and a sample container, wherein each reaction unit has a closed iron core, a primary coil and a secondary coil. The primary coil and secondary coil are, respectively, wound around two sides of the closed iron core, and the secondary coil has an insulation pipe for circulating the reaction medium. When the array induced electric field fluid reaction system operates, no charged needle-type electrodes or electrode plates are inserted into the reaction medium. Electrochemical reaction and metal contamination may be avoided. The reaction units can form an array network connection and series/parallel connection, and when the induced electric field in each reaction unit is acted on the reaction medium, specific reaction effects may be achieved.

10 Claims, 8 Drawing Sheets

(51) Int. Cl.
*G01R 33/44* (2006.01)
*A23F 3/16* (2006.01)
*A23L 3/32* (2006.01)
*A23J 3/00* (2006.01)
*A23L 5/30* (2016.01)
*A23J 3/04* (2006.01)
*A23L 2/50* (2006.01)
*A61L 2/03* (2006.01)
*A61L 2/26* (2006.01)
*B01D 11/02* (2006.01)
*B01J 19/08* (2006.01)
*A23L 3/22* (2006.01)

(52) U.S. Cl.
CPC .............. *A23L 2/50* (2013.01); *A23L 3/32* (2013.01); *A23L 3/325* (2013.01); *A23L 5/30* (2016.08); *A61L 2/03* (2013.01); *A61L 2/26* (2013.01); *B01D 11/0211* (2013.01); *B01J 19/0013* (2013.01); *B01J 19/087* (2013.01); *A23L 3/22* (2013.01); *A23V 2002/00* (2013.01); *B01D 11/0207* (2013.01); *B01J 2219/0072* (2013.01); *B01J 2219/0074* (2013.01); *B01J 2219/00286* (2013.01); *B01J 2219/00306* (2013.01); *B01J 2219/00418* (2013.01); *B01J 2219/00495* (2013.01); *B01J 2219/0803* (2013.01); *B01J 2219/0869* (2013.01); *B01J 2219/0871* (2013.01); *B01J 2219/0877* (2013.01)

(58) Field of Classification Search
CPC ........ B01J 2219/0877; B01J 2219/0072; B01J 2219/00306; B01J 2219/0803; B01J 2219/0074; B01J 2219/00286; B01J 2219/0869; B01J 2219/0871; A23F 3/16; B01D 11/0211; B01D 11/0207; A23J 3/04; A23J 3/00; A23L 3/32; A23L 3/325; A23L 5/30; A23L 2/50; A23L 3/22; A61L 2/26; A61L 2/03; A23V 2002/00
USPC ....... 219/628, 636, 656, 674, 778, 148, 202, 219/209, 497, 121.54, 121.47; 290/53, 290/42, 50; 335/306; 324/318; 345/174
See application file for complete search history.

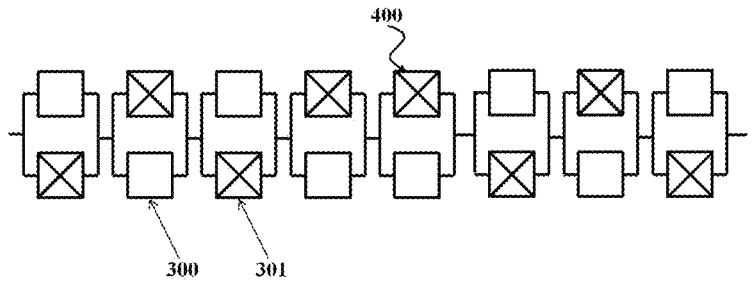

$$U_{2,8} = \begin{bmatrix} 500V & 500V & 500V & 500V & 500V & 500V & 500V & 500V \\ 500V & 500V & 500V & 500V & 500V & 500V & 500V & 500V \end{bmatrix}$$

$$F_{2,8} = \begin{bmatrix} 500Hz & 500Hz & 500Hz & 500Hz & 500Hz & 500Hz & 500Hz & 500Hz \\ 500Hz & 500Hz & 500Hz & 500Hz & 500Hz & 500Hz & 500Hz & 500Hz \end{bmatrix}$$

$$T_{2,8} = \begin{bmatrix} 80°C & 80°C & 80°C & 80°C & 80°C & 80°C & 80°C & 80°C \\ 80°C & 80°C & 80°C & 80°C & 80°C & 80°C & 80°C & 80°C \end{bmatrix}$$

Fig. 7

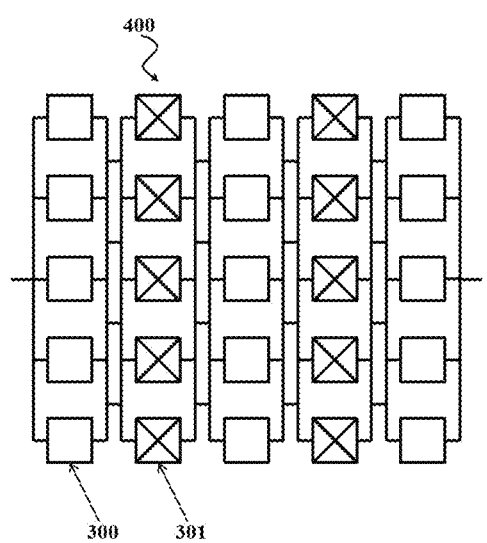

$$U_{5,5} = \begin{bmatrix} 10kV & 10kV & 10kV & 10kV & 10kV \\ 10kV & 10kV & 10kV & 10kV & 10kV \\ 10kV & 10kV & 10kV & 10kV & 10kV \\ 10kV & 10kV & 10kV & 10kV & 10kV \\ 10kV & 10kV & 10kV & 10kV & 10kV \end{bmatrix}$$

$$F_{5,5} = \begin{bmatrix} 45kHz & 45kHz & 45kHz & 45kHz & 45kHz \\ 45kHz & 45kHz & 45kHz & 45kHz & 45kHz \\ 45kHz & 45kHz & 45kHz & 45kHz & 45kHz \\ 45kHz & 45kHz & 45kHz & 45kHz & 45kHz \\ 45kHz & 45kHz & 45kHz & 45kHz & 45kHz \end{bmatrix}$$

$$T_{5,5} = \begin{bmatrix} 60°C & 60°C & 60°C & 60°C & 60°C \\ 60°C & 60°C & 60°C & 60°C & 60°C \\ 60°C & 60°C & 60°C & 60°C & 60°C \\ 60°C & 60°C & 60°C & 60°C & 60°C \\ 60°C & 60°C & 60°C & 60°C & 60°C \end{bmatrix}$$

Fig. 8

$U_{1,10} = [10kV \quad 10kV \quad 10kV \quad 10kV \quad 10kV \quad 10kV \quad 10kV \quad 10kV \quad 10kV \quad 10kV]$ $F_{1,10} = [80kHz \quad 80kHz \quad 80kHz \quad 80kHz \quad 80kHz \quad 80kHz \quad 80kHz \quad 80kHz \quad 80kHz \quad 80kHz]$ $T_{1,10} = [10°C \quad 10°C \quad 10°C \quad 10°C \quad 10°C \quad 10°C \quad 10°C \quad 10°C \quad 10°C \quad 10°C]$

ARRAY INDUCED ELECTRIC FIELD FLUID REACTION SYSTEM AND APPLICATIONS THEREOF

TECHNICAL FIELD

The present invention particularly relates to an array induced electric field fluid reaction system and applications thereof, such as applications in the fields of food processing, sterilization, inactivation of enzyme, protein modification, electrocatalytic reaction, natural compounds extraction, etc.

BACKGROUND

Application regarding continuous-flow tubular reactors in chemical synthesis is a novel reaction technique, which has been developed in the past years. This technology is also being applied in the agro-food processing. A tubular reaction system comprises the following units: mixers, heat exchangers, pumps, reactors, controllers and the like; its pipeline size encompass tens of millimeters to hundreds of microns, thus various reagents during flowing can be quickly and uniformly mixed, thereby demonstrating the outstanding mass transfer and heat transfer performance. Moreover, processing conditions can be conveniently optimized, the increase of production capability also can be achieved, the period required for product output, from research to production, is shortened. On the other hand, it has been reported that various physical fields, such as electric field, sound field, magnetic field, electromagnetic field combined with the tubular reactor was applied for chemical reaction and agro-food processing, causing the change in the mass transfer and reaction kinetic owing to the reaction medium having a specific dielectric properties and magnetic conductive capacity.

Existing electric field technologies containing ohmic heating and pulsed electric field have been widely applied in the food and agriculture. Technical characteristics is that raw materials are located between discharge areas in a channel or chamber, and the sample as a dielectric material is influenced by an alternating electric field at different field intensity and frequency, thereby causing cell electroporation or the change of mass transfer. However, these technologies utilize charged electrodes or electrode plates for the processing, which result in ion polarization, electrochemical reaction, and metal contamination. Therefore, the application of these electrotechnologies is limited, especially in acid and alkaline mediums.

The physical field, such as the magnetic field, sound field, electric field, and electromagnetic field, can be acted as a control parameter of the reaction system. Application of these fields will facilitate or inhibit some chemical reactions. However, the generator of these fields is bulky, sophisticated, and costly. Also, they are not flexibly arranged or installed in a compact system. Thus, applications of these generators as field control units in an array reaction system are limited, which make multi-dimensional reaction condition operation in matrix form impossible.

For instance, the generator of the magnetic field is permanent magnet or Helmholtz coil; the generator of the electromagnetic field is a magnetron equipped with an oscillation generator. The magnetic field and the electromagnetic field acting on inorganic and organic substances can avoid the generator is contact with the reaction medium directly. If the generators of the magnetic field and the electromagnetic field are arranged in an array configuration, the volume of the system may be bulky, and thus the equipment is costly. Moreover, the magnetic field and the electromagnetic field act on the flowing reaction medium in a limited area; the field effect on other location (away from the discharge region) may dissipate. On the other hand, charged electrodes and power supplies as generators of electric fields, makes the electrodes inserted into the reaction medium. Thus, electrode surface corrosion, metal leakage, electrochemical reaction, and sample contamination are inevitable during long-term treatment or vigorous reaction. And, more charged electrodes inserted into the reaction medium in an array configuration may cause serious contamination.

In conclusion, the existing reaction technique cannot effectively utilize the electric fields as control parameter in a matrix form for chemical reaction and agro-food processing.

SUMMARY

In view of the disadvantages in the prior art, the main objective of the present invention is to provide an array induced electric field fluid reaction system and applications thereof.

In order to achieve the objective described above, a technical scheme adopted by the present invention comprises:

embodiments provided by the present invention, wherein an array induced electric field fluid reaction system comprises:

a reaction unit array, including m×n reaction units interactively connected in a network configuration, wherein the m and the n are positive integers larger than 1; each reaction unit comprises:

a closed iron core with a first side and a second side, a primary coil wound around the first side of the closed iron core, and a secondary coil wound around the second side of the closed iron core, wherein the secondary coil comprises an insulation pipe for circulating feed liquid, and the insulation pipe has a sample feeding inlet and a sample discharge outlet;

a power supply connected to the primary coil in each reaction unit providing the excitation voltage for each primary coil;

a feed liquid container in communication with the sample feeding inlet and the sample discharge outlet in the reaction unit array;

wherein, in the reaction unit array, the sample feeding inlet and the sample discharge outlet of the insulation pipe of at least one reaction unit are, respectively, connected to the sample discharge outlet of the insulation pipe of at least one upstream reaction unit and the sample feeding inlet of the insulation pipe of at least one downstream reaction unit, and/or, in the reaction unit array, the sample feeding inlet and the sample discharge outlet of the insulation pipe of at least one reaction unit are, respectively, connected to the sample feeding inlet and the sample discharge outlet of the insulation pipe of at least another reaction unit. Moreover, in the reaction unit array, two winding ends of each primary coil are, respectively, electrically connected to two electrodes (namely a live wire end and a neutral wire end) of the corresponding power supply.

The excitation voltage $U_{m,n}$, the frequency $F_{m,n}$, and the temperature $T_{m,n}$ of the array induced electric field fluid reaction system can be expressed by the following matrixes:

$$U_{m,n} = \begin{bmatrix} u_{11} & u_{12} & \cdots & u_{1n} \\ u_{21} & u_{22} & \cdots & u_{2n} \\ u_{31} & u_{32} & \cdots & u_{3n} \\ \cdots & \cdots & u_{ij} & \cdots \\ u_{m1} & u_{m2} & \cdots & u_{mn} \end{bmatrix} \quad F_{m,n} = \begin{bmatrix} f_{11} & f_{12} & \cdots & f_{1n} \\ f_{21} & f_{22} & \cdots & f_{2n} \\ f_{31} & f_{32} & \cdots & f_{3n} \\ \cdots & \cdots & f_{ij} & \cdots \\ f_{m1} & f_{m2} & \cdots & f_{mn} \end{bmatrix}$$

$$T_{m,n} = \begin{bmatrix} T_{11} & T_{12} & \cdots & T_{1n} \\ T_{21} & T_{22} & \cdots & T_{2n} \\ T_{31} & T_{32} & \cdots & T_{3n} \\ \cdots & \cdots & T_{ij} & \cdots \\ T_{m1} & T_{m2} & \cdots & T_{mn} \end{bmatrix}$$

In the embodiments provided by the present invention, applications of the array induced electric field fluid reaction system in agro-food processing and/or chemical reactions are further provided.

Compared with the prior art, the array induced electric field fluid reaction system provided by the present invention has the corresponding advantages: during this electrical treatment, alternating electric field is induced by alternating magnetic flux, thus electrodes cannot be utilized. No charged electrodes are inserted into the feed liquid (or reaction medium), then ionic polarization, electrochemical reactions, and metal contamination can be avoided. Moreover, these reaction units form a network connection, and the array induced electric field in this fluid reaction system acts on the flowing feed liquid, thereby changing the reaction activation energy and achieving specific reaction kinetics. Meanwhile, the array induced electric field fluid reaction system can be continuously expanded for laboratory-scale, pilot-scale and large-scale production.

BRIEF DESCRIPTION OF THE DRAWINGS

FIG. 7 is a schematic diagram of the arrangement of reaction units and layout of the array induced electric field in embodiment 2;

FIG. 8 is a schematic diagram of the arrangement of reaction units and layout of the array induced electric field in embodiment 3;

Figure 1:
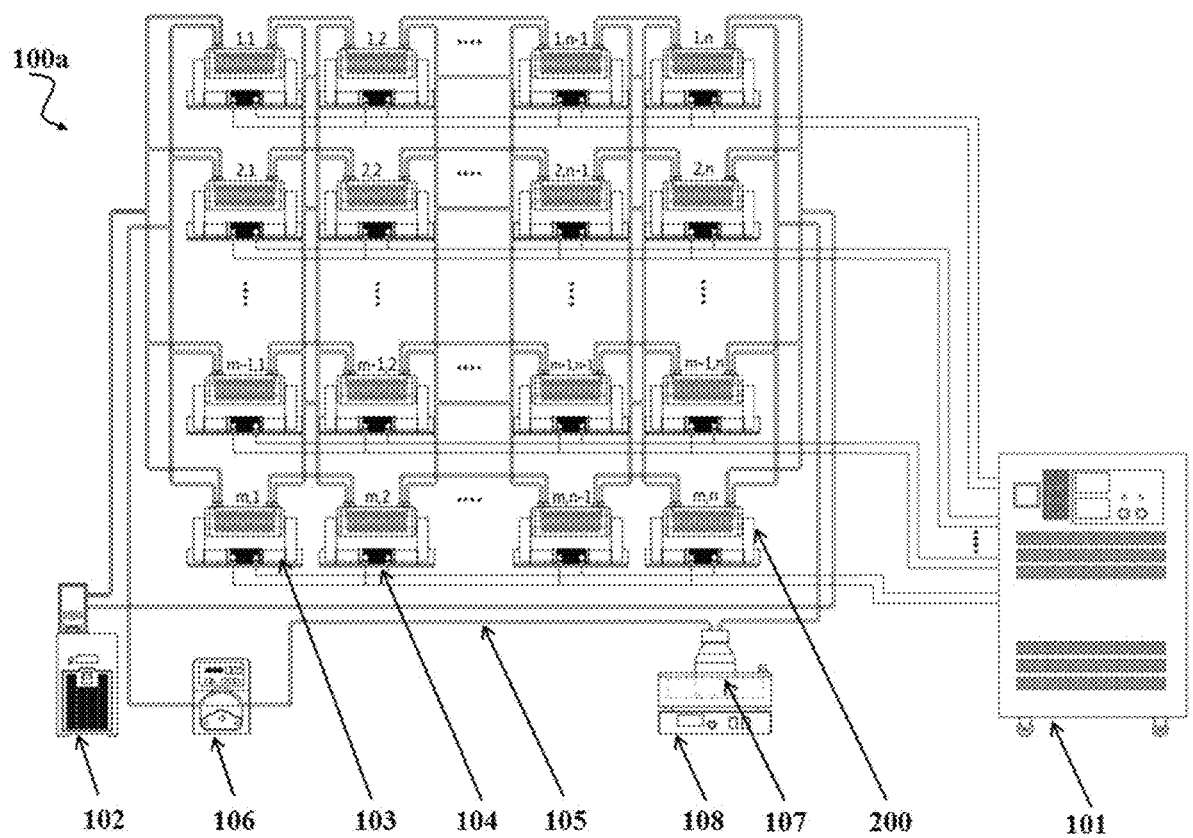
FIG. 1 is a schematic diagram of the array induced electric field fluid reaction system in a closed loop as a typical embodiment provided by the present invention.

In the drawings, the numerical symbols are as follows: 100a—array induced electric field fluid reaction system in a closed loop, 100b—array induced electric field fluid reaction system in an open loop, 101—power supply, 102—constant-temperature circulating bath, 103—closed iron core, 104—primary coil, 105—high-temperature and acid-alkali resistant tube, 106—pump, 107—sample container, 108—constant-temperature bath, 200—reactor, 201—glass spiral tube, 202—constant-temperature jacketed layer, 203—sample feeding inlet, 204—sample discharge outlet, 205—constant-temperature fluid inlet, 206—constant-temperature fluid outlet, 300/301—reaction unit, 400—reaction unit array, 600a—forty reaction units in a series-connection, and 600b—twenty reaction units in a parallel-connection.

DESCRIPTION OF THE EMBODIMENTS

In view of the deficiencies of the prior art, the inventors provide the technical scheme of the present invention based on long-term research and much practice. The present invention achieves specificity effect on agro-food processing and chemical reaction by using array induced electric fields and changes the mass transfer efficiency, reaction kinetic and product yield. The following description further explains the technical scheme and, implementation processes of the invention.

In one aspect, the embodiments are provided by the present invention, wherein an array induced electric field fluid reaction system comprises:

a reaction unit array, including m×n reaction units interactively connected in a network configuration, wherein the m and the n are positive integers larger than 1; each reaction unit comprises:

a closed iron core with a first side and a second side, a primary coil, wound around the first side of the closed iron core, and a secondary coil, wound around the second side of the closed iron core, wherein the secondary coil comprises an insulation pipe for circulating feed liquid (or reaction medium), and the insulation pipe has a sample feeding inlet and a sample discharge outlet;

a power supply, in electric connection with the primary coil of each reaction unit providing the excitation voltage for each primary coil;

a sample container in communication with the sample feeding inlet and the sample discharge outlet in the reaction unit array;

wherein, in the reaction unit array, the sample feeding inlet and the sample discharge outlet of the insulation pipe of at least one reaction unit are, respectively, connected to the sample discharge outlet of the insulation pipe of at least one upstream reaction unit and the sample feeding inlet of the insulation pipe of at least one downstream reaction unit (namely in series connection), and/or, in the reaction unit array, the sample feeding inlet and the sample discharge outlet of the insulation pipe of at least one reaction unit are, respectively, connected to the sample feeding inlet and the sample discharge outlet of the insulation pipe of at least another reaction unit (namely in parallel connection). Moreover, in the reaction unit array, two winding ends of each primary coil are, respectively, electrically connected to two electrodes (namely a live wire and a neutral wire) of the power supply.

Different connection modes between power supply and primary coil cause different polarity of the excitation voltage, resulting in different polarity of the induced electric field in the reaction unit. For instance, the polarity of the excitation voltage is considered as 'positive' when the left winding end of the primary coil is electrically connected to the live wire of the power supply and the right winding end of the primary coil is electrically connected to the neutral wire. Otherwise, the polarity of the excitation voltage is considered as 'negative' when the right winding end of the primary coil is electrically connected to the live wire of the power supply and the left winding end of the primary coil is electrically connected to the neutral wire.

In the reaction unit array, all of the reaction units can be connected in various series-parallel scales according to practical applications.

Each reaction unit is referred to the single-phase transformer structure converting the magnetic energy into the electrical energy and then applying on the reaction medium. When an alternating excitation voltage $U_P$ is applied on the primary coil (the turns of the primary coil is $N_P$), then an alternating magnetic flux is generated within the closed iron core. The magnetic flux density is proportional to the turns of the primary coil. According to Faraday's law of induction and Ampere circuital theorem, alternating voltages $E_S$ and $E_P$ are induced in the secondary coil (the turns of the secondary coil is $N_S$) and the primary coil. $U_S$ is the terminal voltage in the secondary coil. Their relationship is expressed as follows:

$$E_P/E_S = U_P/U_S = N_S/N_P \qquad (1).$$

According to the principle of transformer, when excitation voltage and turns ratio of the primary coil to the secondary coil remain at a fixed level, the induced voltage, namely the intensity of the induced electric field, is also fixed at a constant level.

For instance, in some embodiments, at least parts of the reaction units are in series-connection to each other, that is, the sample feeding inlet and the sample discharge outlet of the insulation pipe of any one reaction unit are, respectively, connected to the sample discharge inlet and the sample feeding outlet of the insulation pipe of another reaction unit.

For instance, in some embodiments, at least parts of the reaction units are in parallel connection to each other, that is, the feeding sample inlet and the sample discharge outlet of the insulation pipe of any one reaction unit are, respectively, connected to the sample feeding outlet and the sample discharge inlet of the insulation pipe of another reaction unit.

For instance, in some embodiments, in the array induced electric field fluid reaction system, a part of the reaction units is in parallel connection to each other and another part of the reaction units is in series connection to each other.

The feed liquid (or reaction medium) can disposable flow through the reaction unit array when the reaction units form an open loop as well as the feed liquid can flow in the reaction unit array circularly when the reaction units form an closed loop during the treatment.

Preferably, all reaction units can be connected by using high-temperature and acid-alkali resistant silicone tube to form the array configuration.

In some preferable embodiments, condition parameters, such as excitation voltage frequency $F_{m,n}$ and temperature $T_{m,n}$ of the array induced electric field fluid reaction system can be expressed by the following matrixes:

$$U_{m,n} = \begin{bmatrix} u_{11} & u_{12} & \cdots & u_{1n} \\ u_{21} & u_{22} & \cdots & u_{2n} \\ u_{31} & u_{32} & \cdots & u_{3n} \\ \cdots & \cdots & u_{ij} & \cdots \\ u_{m1} & u_{m2} & \cdots & u_{mn} \end{bmatrix} \quad F_{m,n} = \begin{bmatrix} f_{11} & f_{12} & \cdots & f_{1n} \\ f_{21} & f_{22} & \cdots & f_{2n} \\ f_{31} & f_{32} & \cdots & f_{3n} \\ \cdots & \cdots & f_{ij} & \cdots \\ f_{m1} & f_{m2} & \cdots & f_{mn} \end{bmatrix}$$

$$T_{m,n} = \begin{bmatrix} T_{11} & T_{12} & \cdots & T_{1n} \\ T_{21} & T_{22} & \cdots & T_{2n} \\ T_{31} & T_{32} & \cdots & T_{3n} \\ \cdots & \cdots & T_{ij} & \cdots \\ T_{m1} & T_{m2} & \cdots & T_{mn} \end{bmatrix}$$

Therefore, during agro-food processing and/or chemical reaction by using the array induced electric field fluid reaction system, multi-dimensional operation may be achieved by adjusting the aforementioned excitation voltage, frequency and temperature matrix parameters.

Matrix is well known in engineering and mathematics. Essentially, the matrix is a plural or real number set arranged in a rectangular array; the numbers $a_{ij}$ with an amount of m×n are arranged in m rows and n columns so as to form an m×n matrix, and the m×n matrix is denoted by $A_{m,n}$:

$$A_{m,n} = \begin{bmatrix} a_{11} & a_{12} & \cdots & a_{1n} \\ a_{21} & a_{22} & \cdots & a_{2n} \\ a_{31} & a_{32} & \cdots & a_{3n} \\ \cdots & \cdots & a_{ij} & \cdots \\ a_{m1} & a_{m2} & \cdots & a_{mn} \end{bmatrix}$$

In addition, the matrix can be transferred into another matrix, such as a transposed matrix $A^T$ and an inverse matrix $A^{-1}$ by the analysis of practical requirements.

In some embodiments, in the reaction unit array, each primary coil is wound around a first direction, and each secondary coil is wound around a first direction or a second direction, wherein the first direction is opposite to the second direction; or, in some embodiments, in the reaction unit array, at least one primary coil is wound in a first direction, at least another primary coil is wound in a second direction, and the secondary coil is wound in the first direction or the second direction, wherein the first direction is opposite to the second direction. The above mentioned first direction is a clockwise direction or a counterclockwise direction.

Specifically, it can be considered that each reaction unit in the array induced electric field fluid reaction system generate 'positive' or 'negative' induced electric field, which can be implemented in the following three ways:

The first way: all primary coils and the power supply are in parallel connection, and the polarity of all excitation voltages are consistent; when the winding directions of all the primary coils in the system are also consistent, the winding of the insulation pipes (secondary coils, referred to as spiral tubes) in the reactors are stipulated to be clockwise or counterclockwise as 'positive' directions so that the opposite direction winding of the insulation pipes in the reactors are stipulated to be 'negative' directions. Then, reaction units include the 'positive' spiral tubes generate 'positive' induced electric fields while reaction units include the 'negative' spiral tubes generate 'negative' induced electric fields.

The second way: all primary coils and the power supply are in parallel connection, and the polarity of all excitation voltages are consistent; when the winding directions of the spiral tubes (secondary coils) in the reactors in the system are also consistent, the winding of the primary coils are stipulated to be clockwise or counterclockwise as 'positive' directions so that the opposite direction winding of the primary coils are stipulated to be 'negative' directions. Then, reaction units include the 'positive' primary coils generate 'positive' induced electric fields, while reaction units include the 'negative' primary coils generate 'negative' induced electric fields.

The third way: the winding directions of the spiral tubes in all reactors in the system are consistent, and the winding directions of all primary coils in the system are also consistent; it is stipulated that the polarity of the excitation voltages act as the 'positive' when the left winding ends of the primary coils are electrically connected to the live wire end of the power supply as well as the right winding ends of the primary coils are electrically connected to the neutral wire end of the power supply. Otherwise, the polarity of the excitation voltages act as the 'negative' when the right winding ends of the primary coils are electrically connected to the live wire end of the power supply as well as the left winding ends of the primary coils are electrically connected to the neutral wire end of the power supply. At this point, reaction units applying the 'positive' excitation voltages generate 'positive' induced electric fields, while reaction units applying the 'negative' excitation voltages generate 'negative' induced electric fields.

Essentially, the reaction units provided by the present invention are arranged in the array configuration, and the condition parameters can be expressed in a matrix form. Furthermore, according to the right-hand screw rule, the reaction units in the system can generate positive and negative induced electric fields by setting the polarity of the excitation voltage and the winding directions of the spiral tubes or primary coils in the reactors, thereby increasing controls multiplicity during the processing.

In some preferable embodiments, the power supply may at least yield sine wave, saw-tooth wave, triangular wave, unipolar pulse and bipolar pulse in a frequency range of 50-1300 Hz or 10-220 kHz with a voltage between 0-200 kV. Therefore, the power supply can excite the primary coils wound around the closed iron cores to generate alternating induced electric fields in the feed liquid.

The closed iron cores are made of at least one of silicon steel, nickel steel or ferrite material.

Furthermore, the primary coils can be made of metal.

In some embodiments, the primary coils are wound around the first side of closed iron cores, the primary coils and the power supply are in parallel-connection that is two winding ends of each primary coil are connected to the two electrodes (namely the live wire end and the neutral wire end) of the power supply.

In some embodiments, each reaction unit comprises a reactor; the insulation pipe is arranged within the reactor, and the two ends of the insulation pipe are exposed from the reactor acting as a sample feeding inlet and a sample discharge outlet.

In some specific embodiments, each insulation pipe is utilized as a supporting tube of the feed liquid (or the secondary coil), and each insulation pipe is wound around the second side of closed iron core as a spiral tube. The two winding ends of each spiral tube, respectively, exposed from the two ends of the corresponding reactor acting as the sample feeding inlet and the sample discharge outlet of the feed liquid. A constant-temperature jacketed layer is arranged outside the spiral tube and is provided with a constant-temperature fluid inlet and a constant-temperature fluid outlet at the two ends of the corresponding reactor, and the constant-temperature fluid inlet and the constant-temperature fluid outlet are used for circulating constant-temperature liquid at different temperatures so as to maintain the temperature of the reactor.

In some specific embodiments, a sample discharge outlet of each reactor is connected to a sample feeding inlet of another reactor and a sample discharge outlet of the other reactor. Vice versa, the sample feeding inlet of each reactor is connected to the sample discharge outlet of another reactor and the sample feeding inlet of the other reactor. That is, all reaction units are mutually communicated end-to-end for forming a network.

Furthermore, a pump can be arranged on a feed liquid mainstream pipeline for driving the reaction medium to flow.

In some embodiments, the array induced electric field fluid reaction system further comprises a temperature-control unit for adjusting the temperature of the constant-temperature liquid.

Preferably, the temperature-control unit comprises a constant-temperature jacketed layer for circulating the constant-temperature liquid. The constant-temperature jacketed layer covers the spiral tube; a constant-temperature fluid inlet and a constant-temperature fluid outlet are located on the constant-temperature jacketed layer of the reactor. The constant-temperature fluid inlet and the constant-temperature fluid outlet on the reactor are further connected to a constant-temperature circulating bath.

The constant-temperature liquid is composed of the fluid at different temperatures, especially the liquid such as water and glycerol, but is not limited thereto.

In some embodiments, the constant-temperature fluid inlet and the constant-temperature fluid outlet of at least one reactor can be, respectively, connected to the constant-temperature fluid outlet of at least one upstream reactor and the constant-temperature fluid inlet of at least one downstream reactor.

In some embodiments, the constant-temperature fluid inlet and the constant-temperature fluid outlet of at least one reactor can be also, respectively, connected to the constant-temperature fluid inlet and the constant-temperature fluid outlet of at least another reactor.

In some specific embodiments, the temperature-control unit may be various constant-temperature circulating baths and constant-temperature baths; an inlet and an outlet on each constant-temperature circulating bath are, respectively, in communication with the constant-temperature fluid inlet and the constant-temperature fluid outlet on each reactor so as to maintain the temperature of the reaction medium during processing; the constant-temperature fluid outlet on each reactor can be connected to the constant-temperature fluid inlet on the next reactor, and the sample container is located in the constant-temperature bath.

Furthermore, the actual power of the power supply ensure each reaction unit work regularly, that is, $P_0 \geq (P_1 + P_2 + \ldots + P_x)$, wherein $P_1$ is the output power of the first reaction unit, $P_2$ is the output power of the second reaction unit, and $P_x$ is the output power of the xth reaction unit; and $P_x = U_P \times I_P = (U_P/Z_P) \times U_P$, wherein the $U_P$ is the excitation voltage of the power supply, $Z_P$ is the impedance of a single primary coil at operating frequency, $I_P$ is the current of the single primary coil, and x is a maximum number of reaction units which can be driven by one power supply.

The number of power supplies may be one or more. Furthermore, multiple power supplies can be arranged in the array induced electric field fluid reaction system per practical requirements.

When the array induced electric field fluid reaction system operate, the reaction medium is considered as a conductor of the secondary coils in all reaction units in which the insulated spiral tubes acts as supporting tubes. The power supply yields an alternating voltage of different waves to excite the primary coils so as to generate an alternating magnetic flux in the closed iron cores. Finally, alternating induced electric fields are generated within the feed liquid in the array induced electric field fluid reaction system; the feed liquid can disposable flow and then pass through the system or can flow in the system circularly during the treatment. Also, during the process, rate of flow, excitation voltage, frequency, wave form, reaction unit array scale and reaction units' connection mode can be set according to the characteristics of the reaction medium and the processing scale.

In the array induced electric field fluid reaction system, the reaction units are connected in the network configuration. Due to the electric field in each reaction unit is induced via alternating magnetic flux; charged electrodes during this electrical treatment can be avoided. Thus, there is no electrode inserted into the reaction medium. The processing scale can be expanded conveniently. The induced electric field, namely the induced voltage, occurs in the spiral tube of each reactor and, per Faraday's law of induction and Thevenin's theorem. The total equivalent induced voltage in the system changes along with the excitation voltage matrix. The impedance of the flowing reaction medium also continuously changes along with the excitation voltage matrix, the frequency matrix and the temperature matrix. Therefore, according to Ohm's law, when the total equivalent voltage of the system acts on the flowing reaction medium with time-varying impedance and electrical conduction, significant effect may be observed during this electrical treatment in the absence of charged electrodes.

In the embodiments provided by the present invention, applications of the array induced electric field fluid reaction system in agro-food processing and/or chemical reactions are further provided.

The chemical reactions comprise at least one of catalysis, synthesis, extraction, hydrolysis, sterilization, inactivation of enzyme and protein modification, but are not limited thereto.

For instance, the array induced electric field fluid reaction system can be applied to assist the organic solvent for extracting edible oil and the like.

Preferably, during the treatment, the power supply can yield sine wave, saw-tooth wave, triangular wave, unipolar pulse and bipolar pulse in a frequency range of 50-1000 Hz with a voltage level between 0-1000 V.

For instance, the array induced electric field fluid reaction system can be applied to sterilization, inactivation of enzyme and protein modification.

Preferably, during the treatment, the power supply is a high voltage power supply, which can yield sine wave, saw-tooth wave, triangular wave, unipolar pulse and bipolar pulse in a frequency range of 20-100 kHz with a voltage level between 0-120 kV.

The following further explain and describe the technical scheme and implementation processes of the present invention through some embodiments in detail.

Embodiment 1: Synthesis of Epoxy Emulsifier

The following describes an application of the array induced electric field fluid reaction system for chemical synthesis using the example of synthesizing an epoxy emulsifier.

As shown in FIG. 1 to FIG. 6, in this embodiment, the present invention provides an array induced electric field fluid reaction system, which comprises a closed loop system 100a (circular flowing) or an open loop system 100b (disposable flowing), reactor 200, reaction unit 300 (or reaction unit 301), reaction unit array 400, forty reaction units in a series-connection 600a, twenty reaction units in a parallel-connection 600b.

Figure 2:
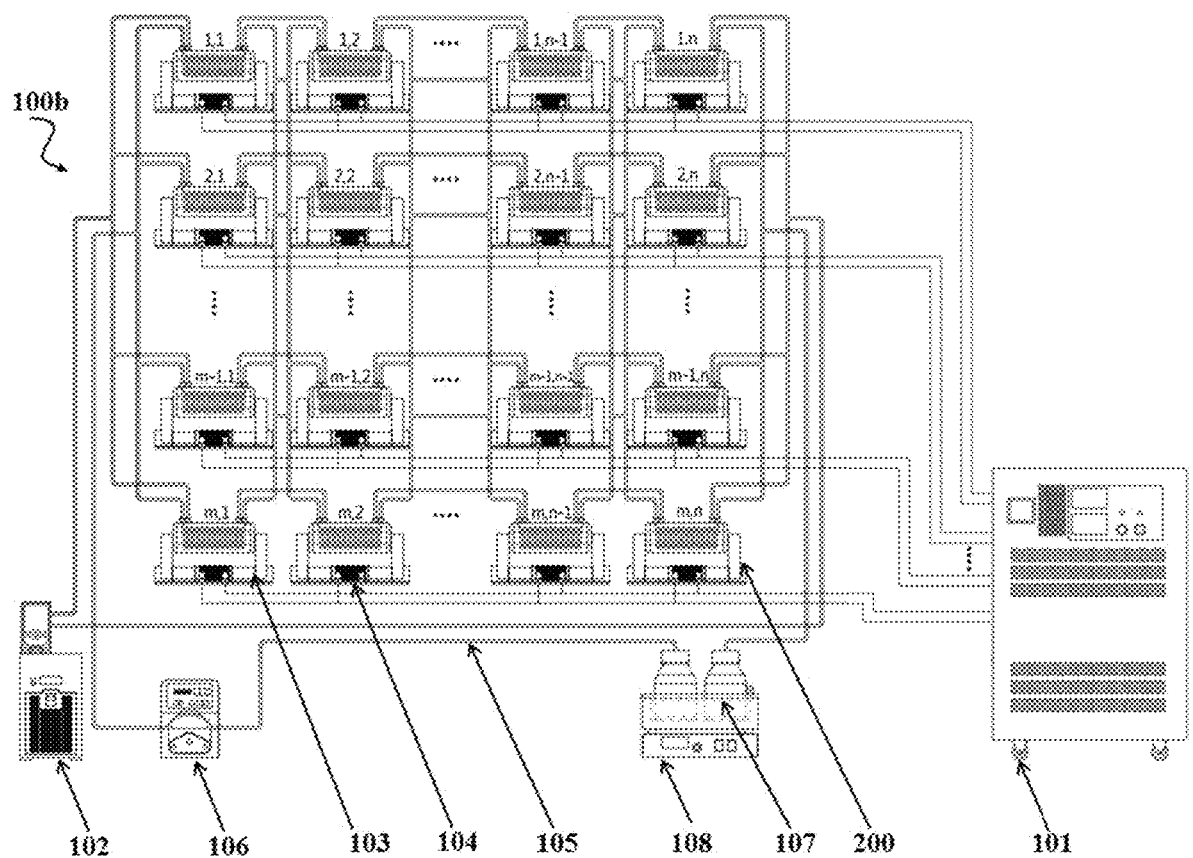
FIG. 2 is a schematic diagram of the array induced electric field fluid reaction system in an open loop as a typical embodiment provided by the present invention.

Referring to FIG. 1 and FIG. 2, the system 100a comprises power supply 101, constant-temperature circulating bath 102, closed iron core 103, primary coil 104, reactor 200, high-temperature and acid-alkali resistant tube 105, pump 106, sample container 107 and constant-temperature bath 108, wherein the power supply 101 is in communication with all primary coils 104; the power supply 101 can yield sine wave, saw-tooth wave, triangular wave, unipolar pulse and bipolar pulse in a frequency range of 50-1300 Hz or 10-220 kHz with a voltage level between 0-200 kV. In each reactor 200, primary coil 104 is a metal coil wound around the first side of the closed iron core 103; the closed iron core 103 is made of silicon steel, nickel steel or ferrite material, and the second side of the closed iron core 103 is wrapped into the reactor 200, thereby ensuring the spiral tube, namely the secondary coil 201, in this reactor 200 is wound around the second side of closed iron core 103.

Figure 3:
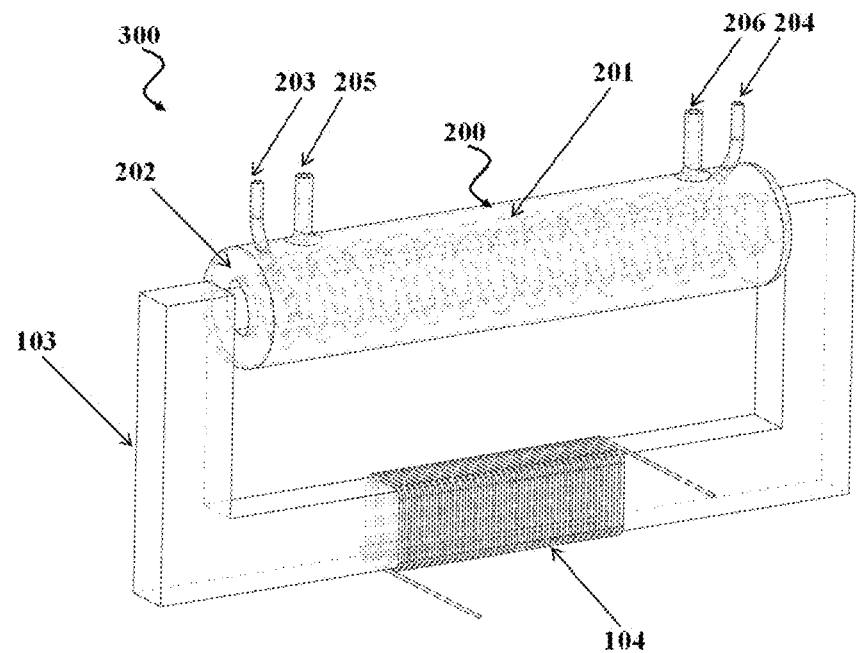
FIG. 3 is a schematic diagram of a reaction unit in a typical embodiment provided by the present invention.

Referring to FIG. 3, one reactor 200 comprises a glass spiral tube 201 as an insulation supporting tube, that is the secondary coil, a constant-temperature jacketed layer 202, a sample feeding inlet 203, a sample discharge outlet 204, a constant-temperature fluid inlet 205 and a constant-temperature fluid outlet 206, wherein the two ends of the glass spiral tube 201 are, respectively, exposed from two ends of the reactor 200 acting as the sample feeding inlet 203 and the sample discharge outlet 204 for circulating the reaction medium. The constant-temperature jacketed layer 202 is arranged outside of the glass spiral tube 201, and the constant-temperature fluid inlet 205 and the constant-temperature fluid outlet 206 are arranged at the two ends of the reactor 200 for circulating constant-temperature liquid at different temperatures to maintain the chemical reaction or agro-food processing temperature.

Figure 4:
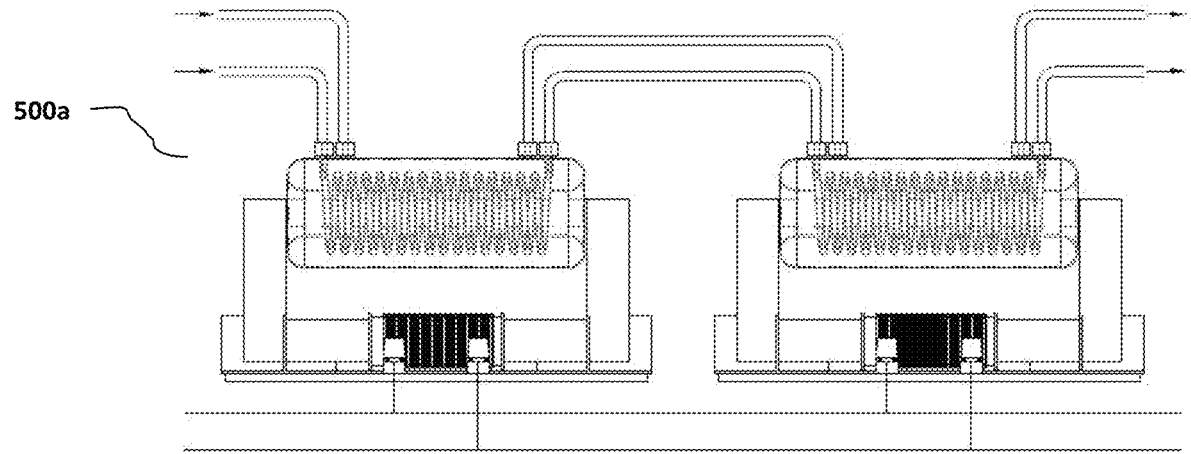
FIG. 4 is a schematic diagram of two reaction units in a series-connection layout as a typical embodiment provided by the present invention.
Figure 5:
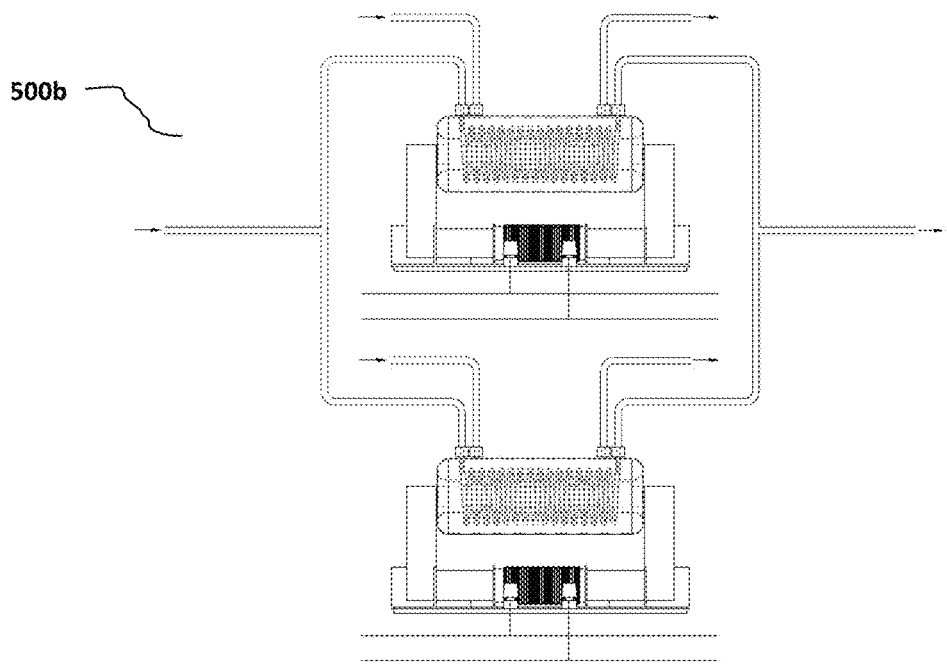
FIG. 5 is a schematic diagram of two reaction units in a parallel-connection layout as a typical embodiment provided by the present invention.

Referring to FIG. 3 again, the reaction unit 300 comprises one reactor 200, one closed iron core 103 and one primary coil 104; the primary coil 104 of each reaction unit 300 is in parallel connection with the power supply 101, and all the reaction units are connected to each other by using high-temperature and acid-alkali resistant tubes 105 to form a series-connection layout, a parallel-connection layout, a series-connection/parallel-connection layout or array configuration in the system. The series-connection layout 500a is: the sample discharge outlet 204 on one reactor 200 is connected to the sample feeding inlet 203 on the next reactor 200, as shown in FIG. 4; the parallel-connection layout 500b is: the sample feeding inlet 203 on one reactor 200 is connected to the sample feeding inlet 203 on the next reactor 200 as well as the sample discharge outlet 204 on the reactor 200 is connected to the sample discharge outlet 204 on the other reactor 200, as shown in FIG. 5; a series-connection/parallel connection layout is: part of the reaction units are in parallel-connection to each other and the other part of the reaction units are in series-connection to each other in the system; the array configuration is: the sample discharge outlet 204 on one reactor 200 is connected to the sample feeding inlet 203 on the next reactor 200, which is also connected to the sample discharge outlet 204 on the other reactor 200, and, vice versa, the sample feeding inlet 203 on one reactor 200 is connected to the sample discharge outlet 204 on another reactor 200 and is also connected with the sample feeding inlet 203 on the other reactor 200, so that all secondary coils, namely the glass spiral tubes 201, are communicated from end-to-end for forming a network. At this point, each secondary coil, namely the glass spiral tube 201, acts as a voltage source. Besides, a pump 106 is arranged on the mainstream pipeline in the system and is connected to the sample container 107 for driving the reaction medium to flow. The sample container is located in the constant-temperature bath 108 for keeping the treatment temperature. Per the practical requirements, the circular flowing treatment (using the closed loop system, FIG. 1) and disposable flowing treatment (using the open loop system, FIG. 2) can be selected.

The actual power of the power supply 101 ensure each reaction unit work regularly, that is, $P_0 \geq (P_1+P_2+ \ldots +P_x)$, wherein $P_1$ is the output power of the first reaction unit, $P_2$ is the output power of the second reaction unit, and $P_x$ is the output power of the xth reaction unit; and $P_x=U_P \times I_P=(U_P/Z_P) \times U_P$, wherein the $U_P$ is the excitation voltage of the power supply, $Z_P$ is the impedance of a single primary coil at operating frequency, $I_P$ is the current of the single primary coil, and x is a maximum number of reaction units which can be driven by one power supply. The power supplies can be added and arranged in the system according to the practical processing scale; the constant-temperature circulating bath 102 is, respectively, in communication with the constant-temperature fluid inlet 205 and the constant-temperature fluid outlet 206 on the reactor 200 for maintaining the reaction temperature. Furthermore, the constant-temperature fluid outlet 206 on each reactor 200 is connected to the constant-temperature fluid inlet 205 on the next reactor 200.

The reaction unit can generate induced electric fields with the polarity of 'positive' or 'negative', which is implemented in the following three ways:

The first way: all primary coils 104 and the power supply 101 are in parallel connection, and the polarity of all excitation voltages are consistent; when the winding directions of all primary coils 104 in the system are also consistent, the winding of the glass spiral tubes 201 in the reactors 200 are stipulated to be clockwise or counterclockwise as 'positive' direction so that the opposite direction winding of the glass spiral tubes 201 are stipulated to be 'negative' direction. Then, reaction units 300 include the 'positive' glass spiral tubes 201 generate 'positive' induced electric fields, while reaction units 301 include the 'negative' glass spiral tubes 201 generate 'negative' induced electric fields.

The second way: all primary coils 104 and the power supply 101 are in parallel connection, and the polarity of all excitation voltages are consistent; when the winding directions of the glass spiral tubes 201 in the reactors 200 in the system are also consistent, the winding of the primary coils 104 are stipulated to be clockwise or counterclockwise as 'positive' directions, so that the opposite direction winding of the primary coils 104 are stipulated to be 'negative' directions. Then, reaction units 300 include the 'positive' primary coils 104 generate 'positive' induced electric fields, and the reaction units 301 include the 'negative' primary coils 104 generate 'negative' induced electric fields.

The third way: the winding directions of the glass spiral tubes 201 in all reactors 200 in the system are consistent, and the winding directions of all primary coils 104 in the system are also consistent; it is stipulated that the polarity of the excitation voltages act as the 'positive' when the left winding ends of the primary coils 104 are electrically connected to the live wire end of the power supply 101 as well as the right winding ends of the primary coils 104 are electrically connected to the neutral wire end of the power supply 101. Otherwise, the polarity of the excitation voltages act as the 'negative' when the right winding ends of the primary coils 104 are electrically connected to the live wire end of the power supply 101 as well as the left winding ends of the primary coils 104 are electrically connected to the neutral wire end of the power supply 101. At this point, reaction units 300 applying 'positive' excitation voltages generate 'positive' induced electric fields, while reaction units 301 applying 'negative' excitation voltages generate 'negative' induced electric fields.

Figure 6:
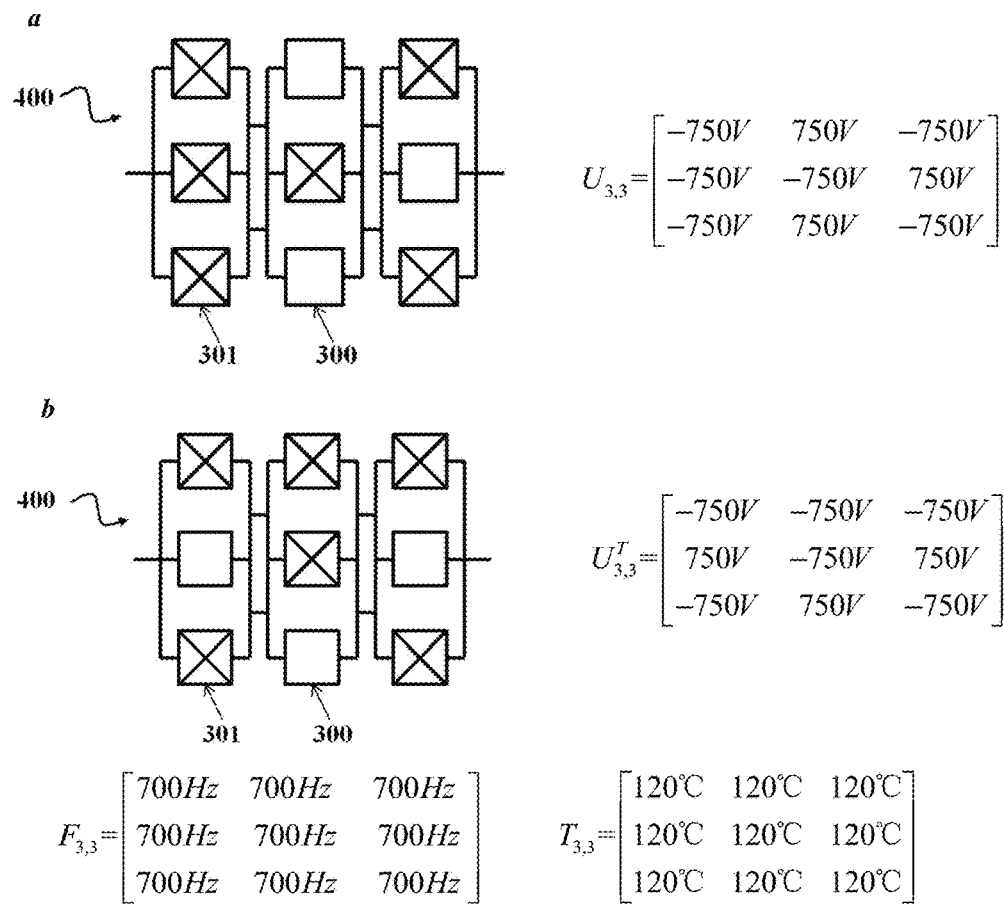
FIG. 6 is a schematic diagram of reaction unit arrangement and layout of the array induced electric field in embodiment 1.

The synthesis of epoxy emulsifier comprises the following steps:

Step 1: setting the reaction unit to generate a 'positive' or 'negative' induced electric field by the third way, wherein the winding of the glass spiral tubes 201 in all reactor 200 are clockwise, and the winding of all primary coils 104 in the system are also clockwise; when the excitation voltage in the reaction unit 300 to be 'positive', the reactor 200 obtains a 'positive' induced electric field, but the excitation voltage in the reaction unit 301 to be 'negative', the reactor 200 obtains a 'negative' induced electric field;

Step 2: 100 g of epoxy resin and 120 g of polyethylene glycol are located into a sample container 107, mixing them uniformly, then adding 3 g of potassium persulfate dropwise;

Step 3: starting the constant-temperature circulating bath 102 and the constant-temperature bath 108 at 120° C. In this embodiment, nine reaction units 300 are utilized, induced electric fields in three reaction units 300 are 'positive', and induced electric fields in the other six reaction units 301 are 'negative'. The reaction time is 120 min. During the beginning 30 min of the reaction, the layout of 'positive' induced electric fields and 'negative' induced electric fields (reaction unit array 400a) in the system is shown in FIG. 6a. In the remaining 90 min of the reaction, the layout of 'positive' induced electric fields and 'negative' induced electric fields (reaction unit array 400b) in the system is shown in FIG. 6b. A circular flowing reaction is applied, that is the system 100a;

Step 4: starting the power supply 101 by using sine waves, wherein the frequency is 700 Hz and the voltage level is 750 V; the matrix of condition parameters are described as: the excitation voltage within the beginning 30 min during the reaction is $U_{3,3}$, the excitation voltage within the remaining 90 min during the reaction is $U_{3,3}^T$. Throughout the process, the frequency is $F_{3,3}$, and the temperature is $T_{3,3}$. All these matrices are shown in FIG. 6. The actual power $P_0$ of each power supply is 10 kW. Moreover, the primary coil 104 wound on the closed nickel-steel core 103 in each reaction unit is excited via the power supply, wherein the central circumference of the closed nickel-steel core 103 is 1050 mm and its thickness is 20 mm. And, the turns of the primary coils 104 in all reaction units is 130, the impedance $Z_p$ of the primary coil 104 is detected to be 750Ω at 700 Hz by an impedance analyzer, the current $I_p$ of each primary coil 104 is 1 A, and the output power of a single reaction unit is $P_n=U_P \times I_P=0.75$ kW. The turns of the glass spiral tube 201, namely the secondary coil, is 25, and the inner diameter of the glass spiral tube 201 is 4 mm. Nine reaction units are utilized, thus the total output power of the system is 6.75 kW ($P_0$=10 kW>$P_1$+$P_2$ ... +$P_8$+$P_9$=6.75 kW) so that one power supply can ensure nine reaction units operating smoothly;

Step 5: starting a pump 106 to driving the reaction medium to flowing in the system circularly at a flow rate of 150 mL/min. After the treatment, stopping the power supply 101, the pump 106, the constant-temperature bath 108 and the constant-temperature circulating bath 102; and Step 6: discharging the reaction medium and measuring its epoxide value according to the hydrochloric acid-acetone method, thereby the epoxide value of 0.643 is obtaining.

Compared to the control, no excitation voltage applied on the primary coils 104, the epoxide value of the medium is 0.353.

Embodiment 2: Hydrolysis of Corn Stalks

The following describes an application of the array induced electric field fluid reaction system for electrocatalysis treatment using the example of hydrolyzing corn stalks.

Step 1: setting the reaction unit to generate a 'positive' or 'negative' induced electric field using the first way, wherein all primary coils 104 and the power supply 101 are in parallel connection, the polarity of the excitation voltage are in 'positive', and the winding of all primary coils 104 in the system are clockwise; when the winding of the glass spiral pipes 201 to be clockwise, the reaction unit 300 obtains a 'positive' induced electric field, but when the winding of the glass spiral pipes 201 to be counterclockwise, the reaction unit 301 obtains a 'negative' induced electric field;

Step 2: 2000 g of 60 meshes corn stalk powder are located into an 50 L sample container 107, adding 30 L distilled water, using 1 mol/L HCl to adjust pH of the reaction medium at 1.2, and mixing it uniformly;

Step 3: starting the constant-temperature circulating bath 102 and the constant-temperature bath 108 at 80° C. In this embodiment, sixteen reaction units 300 are utilized; the winding of the glass spiral tubes 201 in eight reaction units 300 are clockwise, and the winding of the glass spiral tubes 201 in other eight reaction units 301 are counterclockwise. Thus, induced electric fields in eight reaction units 300 are 'positive', and induced electric fields in the other eight reaction units 301 are 'negative'. The layout of 'positive' induced electric fields and 'negative' induced electric fields (reaction unit array 400) in the system is shown in FIG. 7. And, a circular flowing reaction is applied, that is the system 100a;

Step 4: starting the power supply 101 by using sine wave, wherein the frequency is 500 Hz and the voltage level is 500 V; the matrix of the condition parameters are described as: the excitation voltage is $U_{2,8}$, the voltage frequency is $F_{2,8}$, and the temperature is $T_{2,8}$. All these matrices are as shown in FIG. 7. The actual power $P_0$ of each power supply is 20 kW. And, the primary coil 104 wound on the closed nickel-steel core 103 in each reaction unit is excited via the power supply, wherein the central circumference of the closed nickel-steel core 103 is 1050 mm and its thickness is 20 mm. And, the turns of the primary coils 104 in all reaction units is 200, the impedance $Z_p$ of the primary coil 104 is detected to be 250Ω at 500 Hz by an impedance analyzer, the current $I_p$ of each primary coil 104 is 2 A, and the output power of a single reaction unit is $P_n$=$U_p$×$I_p$=1 kW; the turns of the glass spiral tube 201, namely the secondary coil, is 25, and the inner diameter of the glass spiral tube 201 is 3 mm. Sixteen reaction units are utilized, thus the total output power of the system is 16 kW ($P_0$=20 kW>$P_1$+$P_2$ ... $P_{15}$+$P_{16}$=16 kW) so that one power supply can ensure sixteen reaction units operating smoothly;

Step 5: starting a pump 106 for driving the reaction medium flowing in the system circularly at a flow rate of 500 mL/min. The treatment time is 8 hour. After the treatment, stopping the power supply 101, the pump 106, the constant-temperature bath 108 and the constant-temperature circulating bath 102; and Step 6: discharging the reaction medium, cooling it to reach room temperature, subsequently adding 1% $NaHCO_3$ solution into the medium to adjust the pH level to 7, stopping the reaction and centrifuging the medium at 5000 rpm for 30 min in order to remove sediments, thereby obtaining the hydrolysate, which includes the reducing sugar.

After the measurement, reducing sugar content of the obtained hydrolysate is 45.4 g/L. Compared to the control, no excitation voltage is applied on the primary coils 104, reducing sugar content of the obtained hydrolysate is just 5.3 g/L.

Embodiment 3: Extraction of Pectin from Apple Pomace

The following further describes an application regarding the array induced electric field fluid reaction system in electric-field-assisted extraction using the example of extracting pectin from apple pomace.

Step 1: setting the reaction unit to generate a 'positive' or 'negative' induced electric field by using the first way, wherein all primary coils 104 and the power supplies 101 are in parallel connection, the polarity of the excitation voltage are in 'positive', and the winding of all primary coils 104 in the system are clockwise; when the winding of the glass spiral pipes 201 to be clockwise, the reaction unit 300 obtains a 'positive' induced electric field, but when the winding of the glass spiral pipes 201 to be counterclockwise, the reaction unit 301 obtains a 'negative' induced electric field;

Step 2: 2000 g of apple, pulping and placing them into a 50 L sample container 107; adding 35 L distilled water then mixing uniformly; using 1 mol/L HCl to adjust the pH of the medium to 1.5;

Step 3: starting the constant-temperature circulating bath 102 and the constant-temperature bath 108 at 60° C. In this embodiment, twenty-five reaction units are utilized, the winding of the glass spiral tubes 201 in fifteen reaction units 300 are clockwise, and the winding of the glass spiral tubes 201 in the other ten reaction units 301 are counterclockwise. Thus, induced electric fields in fifteen reaction units 300 are 'positive', and induced electric fields in the other ten reaction units 301 are 'negative'. The layout of 'positive' induced electric fields and 'negative' induced electric fields (reaction unit array 400) in the system is shown in FIG. 8. Also, a disposable flowing reaction is applied, that is the system 100b;

Step 4: starting the power supplies 101 by using sine wave, wherein the frequency is 45 kHz and the voltage level is 10 kV; the matrix of the condition parameters are described as: the excitation voltage is $U_{5,5}$, the frequency is $F_{5,5}$, and the temperature is $T_{5,5}$. All these matrices are shown in FIG. 8. The actual power $P_0$ of each power supply is 40 kW. And, the primary coil 104 wound on the closed nickel-steel core 103 in each reaction unit is excited via the power supply, wherein the central circumference of the closed nickel-steel core 103 is 850 mm, and its thickness is 28 mm. The turns of the primary coils 104 in all reaction units is 110, the impedance $Z_p$ of the primary coil 104 is detected to be 25 kΩ at 45 kHz by an impedance analyzer, the current $I_p$ of each primary coil 104 is 0.4 A, and the output power of a single reaction unit is $P_n=U_P \times I_P=4$ kW. The turns of the glass spiral tube 201, namely the secondary coil, is 23, and the inner diameter of the glass spiral tube 201 is 4 mm. Twenty-five reaction units are utilized, that is the total output power of the system is 100 kW (according to $P_0+P_0+P_0=120$ kW$>P_1+P_2 \ldots +P_{24}+P_{25}=100$ kW) so that three power supplies can ensure all twenty-five reaction units operating smoothly;

Step 5: starting a pump 106 for driving the reaction medium disposable flowing and then passes through the system at a flow rate of 500 mL/min. The total reaction time is 85 min. After the treatment, stopping the power supplies 101, the pump 106, the constant-temperature bath 108 and the constant-temperature circulating bath 102; and Step 6: discharging the reaction medium, cooling it to reach room temperature, subsequently adding 1% NaHCO$_3$ solution into the medium to adjust the pH level to 7, then stopping the reaction, centrifuging the medium at 3000 rpm for 15 min in order to remove sediments, and finally drying the filtrate in an air drying oven at 48° C. for 15 h, thereby obtaining the pectin powder.

After the measurement, the mass of the obtained pectin from apple pomace by using the array induced electric field fluid reaction system is 306.5 g. Compared to the control, no excitation voltage is applied on the primary coils 104, and the mass of the obtained pectin is just 76.5 g.

Embodiment 4: Extraction of Grape Seed Oil

The following describes an application of the array induced electric field fluid reaction system for edible oil extraction treatment using the example of extracting grape seed oil.

Figure 9:
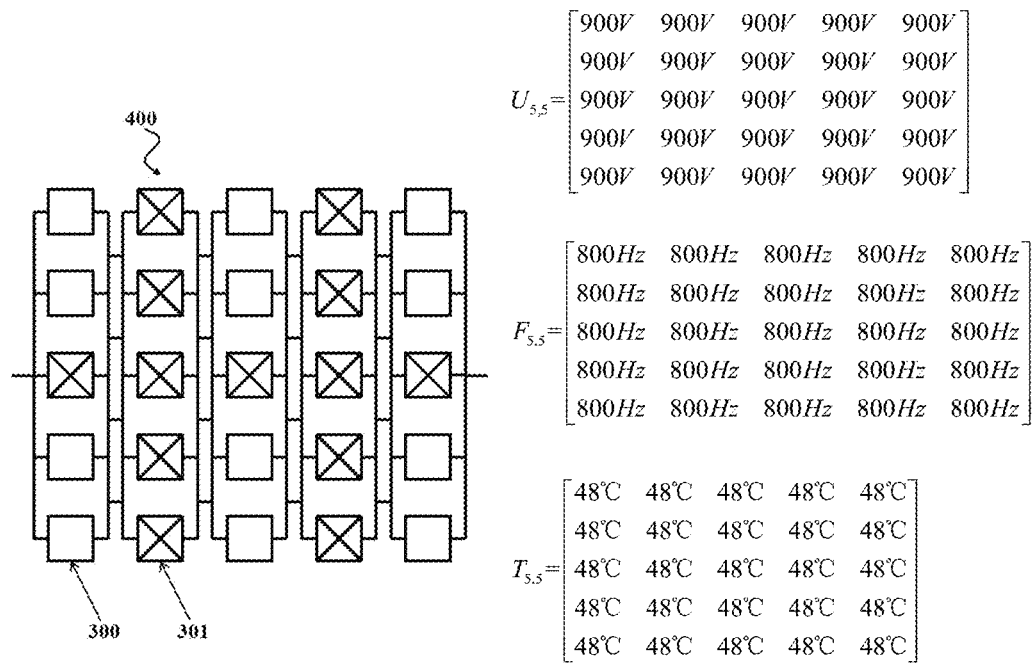
FIG. 9 is a schematic diagram of the arrangement of reaction units and layout of the array induced electric field in embodiment 4.

The extraction of grape seed oil comprises the following steps:

Step 1: setting the reaction unit to generate a 'positive' or 'negative' induced electric field using the second way, wherein all primary coils 104 and the power supplies 101 are in parallel connection, the polarity of all excitation voltage are 'positive', and the winding of the glass spiral tubes 201 in the reactors 200 are clockwise; Thus, a 'positive' induced electric field appeared in the reaction unit 300 with the primary coil 104 of clockwise winding, and a 'negative' induced electric field appeared in the reaction unit 301 with the primary coil 104 of counterclockwise winding;

Step 2: 10 kg of 60 meshes grape seed oil are located into an 200 L sample container 107, taking n-hexane as the extractant, then adding the extractant into the sample container 107, and mixing the reaction medium uniformly;

Step 3: starting the constant-temperature circulating bath 102 and the constant-temperature bath 108 at 48° C. In this embodiment, twenty-five reaction units are utilized; the winding of the primary coils 104 in twelve reaction units 300 are clockwise, and the winding of the primary coils 104 in the other thirteen reaction units 301 are counterclockwise. Thus, induced electric fields in twelve reaction units 300 are 'positive', and induced electric fields in the other thirteen reaction units 301 are 'negative'. The layout of 'positive' induced electric fields and 'negative' induced electric fields (reaction unit array 400) in the system is shown in FIG. 9. Also, a disposable flowing reaction is applied, that is the system 100b;

Step 4: starting the power supplies 101 by using saw-tooth wave, wherein the frequency is 800 Hz and the voltage level is 900 V. The matrix of the condition parameters are described as: the excitation voltage is $U_{5,5}$, the frequency is $F_{5,5}$, and the temperature is $T_{5,5}$. All these matrices are shown in FIG. 9. The actual power $P_0$ of each power supply is 50 kW. And, the primary coil 104 wound on the closed nickel-steel core 103 in each reaction unit is excited via the power supply, wherein the central circumference of the closed nickel-steel core 103 is 1050 mm, and its thickness is 20 mm. The turns of the primary coils 104 in all reaction units is 120, the impedance $Z_p$ of the primary coil 104 is detected to be 300Ω at 800 Hz by an impedance analyzer, the current $I_p$ of each primary coil 104 is 3 A, and the output power of a single reaction unit is $P_n=U_P \times I_P=2.7$ kW. The turns of the glass spiral tube 201, namely the secondary coil, is 23, and the inner diameter of the glass spiral tube 201 is 4 mm. Twenty-five reaction units are utilized, thus the total output power of the system is 67.5 kW ($P_0+P_0=100$ kW$>P_1+P_2 \ldots +P_{24}+P_{25}=67.5$ kW) so that two power supplies can ensure all twenty-five reaction units operating smoothly;

Step 5: starting a pump 106 for driving the reaction medium disposable flowing and then passes through the system at a flow rate of 5 L/min. The total reaction time is 33 min. After the treatment, stopping the power supplies 101, the pump 106, the constant-temperature bath 108 and the constant-temperature circulating bath 102; and Step 6: discharging the reaction medium and filtering it, thereby separating grape seed residues from the extractant by using a rotary evaporator at 55° C. for recycling the n-hexane, thereby obtaining grape seed oil with a mass of 1458 g. Compared to the control, no excitation voltage is applied on the primary coils 104, and the mass of the obtained grape seed oil is just 563 g.

Embodiment 5: Sterilization and Enzyme Inactivation of Apple Juice

The following describes an application of the array induced electric field fluid reaction system for liquid food sterilization and inactivation of enzyme using the example of killing *Escherichia coli* and inactivating polyphenol oxidase in apple juice.

Figure 10:
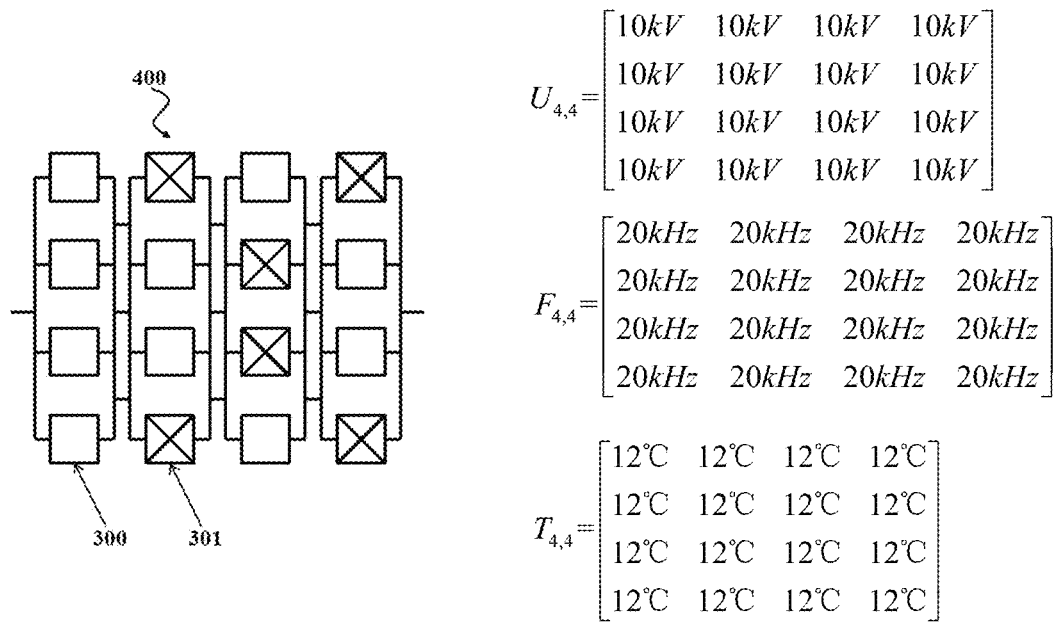
FIG. 10 is a schematic diagram of the arrangement of reaction units and layout of the array induced electric field in embodiment 5.

The sterilization and enzyme inactivation of apple juice comprises the following steps:

Step 1: setting the reaction unit to generate a 'positive' or 'negative' induced electric field using the second way, wherein all primary coils 104 and the power supplies 101 are in parallel connection, the polarity of the excitation voltage are 'positive', and the winding of the glass spiral tubes 201 in the reactors 200 are in clockwise; Thus, a 'positive' induced electric field appeared in the reaction unit 300 with the primary coil 104 of clockwise winding, and a 'negative' induced electric field appeared in the reaction unit 301 with the primary coil 104 of counterclockwise winding;

Step 2: washing the apples, peeling them and cutting into blocks of 2 cm×2 cm×2 cm; putting these blocks into an electric juicer, wherein 0.1% vitamin C is added into the machine to prevent the browning during the squeezing; centrifuging the squeezed apple pulp at 8000 rpm for 20 min, and then filtering supernatant by using two layers of gauze, thereby obtaining original apple juice sample; and sterilizing at 121° C. for 20 min for preparing the bacteria-containing apple juice sample;

Step 3: taking *Escherichia coli* (CGMCC 1.90) as the target microorganism, and preparing them by taking the following steps: firstly, performing activation culture on test-tube strain, namely, preparing nutrient agar medium to conduct slant culture; secondly, inoculating the strain into nutrient broth at 35° C. for 13 h while ensuring the cell concentration at a level of $10^8$-$10^9$ cfu/mL. Then, inoculating the above 6 mL of culture solution into 600 mL sterilized apple juice while ensuring the cell concentration in the sample at a level of $10^6$-$10^7$ cfu/mL, thereby obtaining the bacteria-containing apple juice sample;

Step 4: preparing polyphenol oxidase crude extract: mixing 100 mL the apple juice sample (not treated by 121° C. sterilization) and 400 mL acetone, then the mixture is pre-cooled at −26° C.; performing vacuum filtration on the mixture, thereby obtaining sediment; blowing away residual acetone in the sediment by using cold air; and solving the obtained sediment in 150 mL of 0.05 mol/L phosphate buffer solution (pH=6.5) again, then stirring for 30 min, and centrifuging the solution, thereby obtaining the supernatant, which is the polyphenol oxidase crude extract;

Step 5: taking 5 L of the original apple juice sample and the bacteria-containing apple juice sample into a sample container 107, respectively;

Step 6: starting the constant-temperature circulating bath 102 and the constant-temperature bath 108 at 12° C. In this embodiment, sixteen reaction units are utilized; the winding of the primary coils 104 in the ten reaction units 300 are clockwise, and the winding of the primary coils 104 in the other six reaction units 301 are counterclockwise. Thus, induced electric fields in ten reaction units 300 are 'positive', and induced electric fields in the other six reaction units 301 are 'negative'. The layout of 'positive' induced electric fields and 'negative' induced electric fields (reaction unit array 400) in the system is shown in FIG. 10. Also, a disposable flowing reaction is utilized, that is the system 100b;

Step 7: starting the power supplies 101 by using sine wave, wherein the frequency is 20 kHz and the voltage level is 10 kV; the matrix of condition parameters are described as: the excitation voltage is $U_{4,4}$, the frequency is $F_{4,4}$, and the temperature is $T_{4,4}$. All these matrices are shown in FIG. 10. The actual power $P_0$ of each power supply is 40 kW. And, the primary coil 104 of the closed nickel-steel core 103 in each reaction unit is excited via the power supply, wherein the central circumference of the closed nickel-steel core 103 is 850 mm, and its thickness is 28 mm. The turns of the primary coils 104 in all reaction units is 100, the impedance $Z_p$ of the primary coil 104 is detected to be 20 kΩ at 20 kHz by an impedance analyzer, the current $I_p$ of each primary coil 104 is 0.5 A, and the output power of a single reaction unit is $P_n = U_P \times I_P = 5$ kW. The turns of the glass spiral tube 201, namely the secondary coil, is 25, and the inner diameter of the glass spiral tube 201 is 2 mm. Sixteen reaction units are utilized, thus the total output power of the system is 80 kW $(P_0+P_0+P_0=120 \text{ kW} > P_1+P_2 \ldots P_{15}+P_{16}=80 \text{ kW})$ so that two power supplies can ensure all sixteen reaction units operating smoothly;

Step 8: starting a pump 106 for driving the reaction medium disposable flowing and passes through the system at a flow rate of 2 L/min. The total reaction time is 3 min. After the treatment, stopping the power supply 101, the pump 106, the constant-temperature bath 108 and the constant-temperature circulating bath 102; and Step 9: discharging the original apple juice sample and the bacteria-containing apple juice sample, respectively, conducting polyphenol oxidase activity determination and *Escherichia coli* determination according to the method of AOAC 991.14; colony counting is conducted on the treated sample; sterilization effect is represented by the lethal dose, and the calculation formula of the lethal dose (LD) is as follows:

$$LD = \log(N_0/N)$$

In the above formula: N is the number of microorganisms after processing with the unit of cfu/mL; the $N_0$ is the number of microorganisms before processing with the unit of cfu/mL; polyphenol oxidase activity determination is described as follows: 2 mL buffer solution at pH 4.3 and 0.7 mL of catechol solution are added into a colorimetric cup and are stirred; 0.3 mL polyphenol oxidase crude extract is added into the mixture. The absorption value of the mixture at 400 nm is determined by using a spectrophotometer. The unit of enzyme activity is defined as follows: the absorption value at 400 nm increasing one unit per minute is defined as one enzyme activity unit, and thus the relative enzyme activity of polyphenol oxidase (%)=enzyme activity after the treatment/enzyme activity before the treatment×100%.

After the determination, the colony number of *Escherichia coli* in the bacteria-containing apple juice sample is reduced by 4.3 LD, and the relative enzyme activity of polyphenol oxidase in the original apple juice sample is 26.5%, treated by the array induced electric field fluid reaction system respectively.

Compared to the control, no excitation voltage is applied on the primary coils 104, and the relative enzyme activity of the obtained polyphenol oxidase in the original apple juice sample as well as the colony number of the obtained *Escherichia coli* in the bacteria-containing apple juice sample are not remarkably different from those before processing (P<0.05).

Embodiment 6: Extraction of Orange Peel Oil

The following further describes an application of the array induced electric field fluid reaction system for peel oil extraction using the example of extracting orange peel oil.

Figure 11:
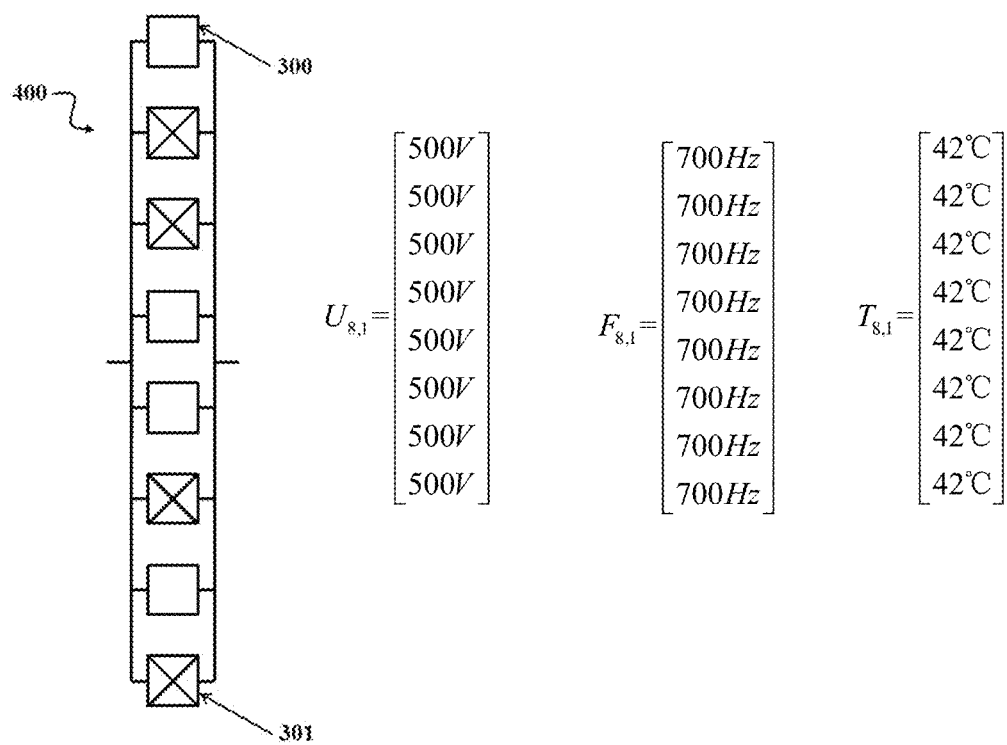
FIG. 11 is a schematic diagram of the arrangement of reaction units and layout of the array induced electric field in embodiment 6.

The extraction of orange peel oil comprises the following steps:

Step 1: setting the reaction unit to generate a 'positive' or 'negative' induced electric field using the second way, wherein all primary coils 104 and the power supplies 101 are in parallel connection, the polarity of the excitation voltage are 'positive', and the winding of the glass spiral tubes 201 in the reactors 200 are clockwise; Thus, a 'positive' induced electric field appeared in the reaction unit 300 with the primary coil 104 of clockwise winding, and a 'negative' induced electric field appeared in the reaction unit 301 of with the primary coil 104 of counterclockwise winding;

Step 2: 2 kg of 80 meshes orange peel powder are located into a 50 L sample container 107, taking petroleum ether as the extractant, adding the extractant into the container 107, and mixing the reaction medium uniformly;

Step 3: starting the constant-temperature circulating bath 102 and the constant-temperature bath 108 at 42° C. In this embodiment, eight reaction units are utilized; the winding of the primary coils 104 in the four reaction units 300 are clockwise, and the winding of the primary coils 104 in the other four reaction units 301 are counterclockwise. Thus, induced electric fields in four reaction units 300 are 'positive', and induced electric fields in the other four reaction units 301 are 'negative'. The layout of 'positive' induced electric fields and 'negative' induced electric fields (reaction unit array 400) in the system is shown in FIG. 11. Also, a circular flowing reaction is applied, that is the system 100a;

Step 4: starting the power supply 101 by using sine wave, wherein the frequency is 700 Hz and the voltage level is 500 V. The matrix of the condition parameters are described as: the excitation voltage is $U_{8,1}$, the frequency is $F_{8,1}$, and the temperature is $T_{8,1}$. All these matrices are shown in FIG. 11. The actual power $P_0$ of each power supply is 10 kW. And, the primary coil 104 wound on the closed nickel-steel core 103 in each reaction unit 300 is excited via the power supply, wherein the central circumference of the closed nickel-steel core 103 is 1050 mm, and its thickness is 20 mm. The turns of the primary coils 104 in all the reaction units is 100, the impedance $Z_p$ of the primary coil 104 is detected to be 250Ω at 700 Hz by an impedance analyzer, the current $I_p$ of each primary coil 104 is 2 A, and the output power of a single reaction unit is $P_n=U_P\times I_P=1$ kW. The turns of the glass spiral tube 201, namely the secondary coil, is 20, and the inner diameter of the glass spiral tube 201 is 3 mm. Eight reaction units are utilized, thus the total output power of the system is 8 kW $P_0=10$ kW$>P_1+P_2\ldots+P_7+P_8=8$ kW) so that one power supply can ensure all eight reaction units operating smoothly;

Step 5: starting a pump 106 for driving the reaction medium flowing in the system circularly at a flow rate of 1 L/min. The total reaction time is 15 min. After the treatment, stopping the power supply 101, the pump 106, the constant-temperature bath 108 and the constant-temperature circulating bath 102; and Step 6: discharging the reaction medium and filtering the liquid, thereby separating orange peel residues from the extractant; and performing vacuum rotary evaporation on the liquid at 52° C. for recycling the petroleum ether, thereby obtaining orange peel oil with a mass of 213 g. Compared to the control, no excitation voltage is applied on the primary coils 104, and then the mass of the obtained orange peel oil is just 63 g.

Embodiment 7: Electrical Treatment of Egg Whites

The following describes an application of the array induced electric field fluid reaction system for protein modification using the example of changing foaming property and foaming stability before and after this electrical treatment.

Figure 12:
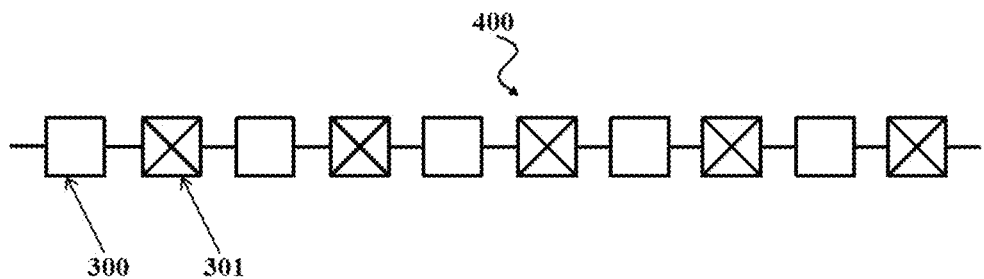
FIG. 12 is a schematic diagram of the arrangement of reaction units and layout of the array induced electric field in embodiment 7.

The electrical treatment of egg whites comprises the following steps:

Step 1: setting the reaction unit to generate a 'positive' or 'negative' induced electric field using the second way, wherein all primary coils 104 and the power supplies 101 are in parallel connection, the polarity of the excitation voltage are 'positive', and the winding of the glass spiral tubes 201 in the reactors 200 are clockwise; Thus, a 'positive' induced electric field appeared in the reaction unit 300 with the primary coil 104 of clockwise winding, and a 'negative' induced electric field appeared in the reaction unit 301 with the primary coil 104 of counterclockwise winding;

Step 2: taking the eggs and placing them into a water bath at 30° C., washing the eggshells, then separating the egg yolk from the egg white, and mixing the egg white uniformly by using an electronic stirrer at 100 r/min, thereby obtaining the egg white solution as the sample;

Step 3: 6 L of the prepared sample are located in a sample container 107;

Step 4: starting the constant-temperature circulating bath 102 and the constant-temperature bath 108 at 10° C. In this embodiment, ten reaction units are utilized; the winding of the primary coils 104 in the five reaction units 300 are clockwise, and the winding of the primary coils 104 in the other five reaction units 301 are counterclockwise. Thus, induced electric fields in five reaction units 300 are 'positive', and induced electric fields in the other five reaction units 301 are 'negative'. The layout of 'positive' induced electric fields and 'negative' induced electric fields (reaction unit array 400) in the system is shown FIG. 12. Also, a disposable flowing reaction is utilized, that is the system 100b;

Step 5: starting the power supplies 101 by using sine wave, wherein the frequency is 80 kHz and the voltage level is 10 kV; the matrix of the condition parameters are described as: the excitation voltage is $U_{1,10}$, the frequency is $F_{1,10}$, and the temperature is $T_{1,10}$. All these matrices are as shown in FIG. 12. The actual power $P_0$ of each power supply is 20 kW. And, the primary coil 104 wound on the closed nickel-steel core 103 in each reaction unit is excited via power supplies, wherein the central circumference of the closed nickel-steel core 103 is 950 mm, and its thickness is 25 mm. The turns of the primary coils 104 in all the reaction units is 100, the impedance $Z_p$ of the primary coil 104 is detected to be 40 kΩ at 700 Hz by an impedance analyzer, the current $I_p$ of each primary coil 104 is 0.25 A, and the output power of the single reaction unit is $P_n=U_P\times I_P=2.5$ kW. The turns of the glass spiral tube 201, namely the secondary coil, is 24, and the inner diameter of the glass spiral tube 201 is 3 mm. Ten reaction units are utilized, thus the total output power of the system is 25 kW ($P_0+P_0=40$ kW$>P_1+P_2\ldots+P_9+P_{10}=25$ kW) so that two power supplies can ensure all ten reaction units operating smoothly;

Step 6: starting a pump 106 for driving the reaction medium disposable flowing and passes through the system at a flow rate of 500 mL/min. The total reaction time is 15 min. After the treatment, stopping the power supplies 101, the pump 106, the constant-temperature bath 108 and the constant-temperature circulating bath 102; and Step 7: discharging the egg white solution to for determining foaming property and foaming stability; referring to the SATHE method by diluting the egg white via deionized water till its mass content is 2%; and taking 100 mL of diluted egg white solution and dispersing the solution at 10,000 r/min for 2 min by using a high-speed homogenizer; then recording the foam volume $V_1$ (when the homogenization stops immediately) and $V_2$ (30 min after the homogenization stops); finally calculating the foaming property and the foaming stability by the following formulae:

$$\text{foaming property}/\%=(V_1/100)\times 100$$

$$\text{foaming stability}/\%=(V_2/V_1)\times 100$$

The determination of the foaming property and the foaming stability is according to the following article:

SATHE S K. Functional properties of the great northern bean proteins: emulsion, foaming, viscosity and gelation properties [J]. Journal of Food Science, 1981, 46(1): 71-74.

After the determination, the foaming property and the foaming stability of the egg whites solution treated the array induced electric fields are, respectively, 127.4% and 88.3%. Compared to the control, no excitation voltage is applied on the primary coils 104, and the foaming property as well as the foaming stability of the egg white solution is, respectively, 87.4% and 68.3%.

Embodiment 8: Extraction of Shiny-Leaved Yellow Horn Oil

The following describes an application of the array induced electric field fluid reaction system for edible oil extraction treatment using the example of extracting shiny-leaved yellow horn oil.

Figure 13:
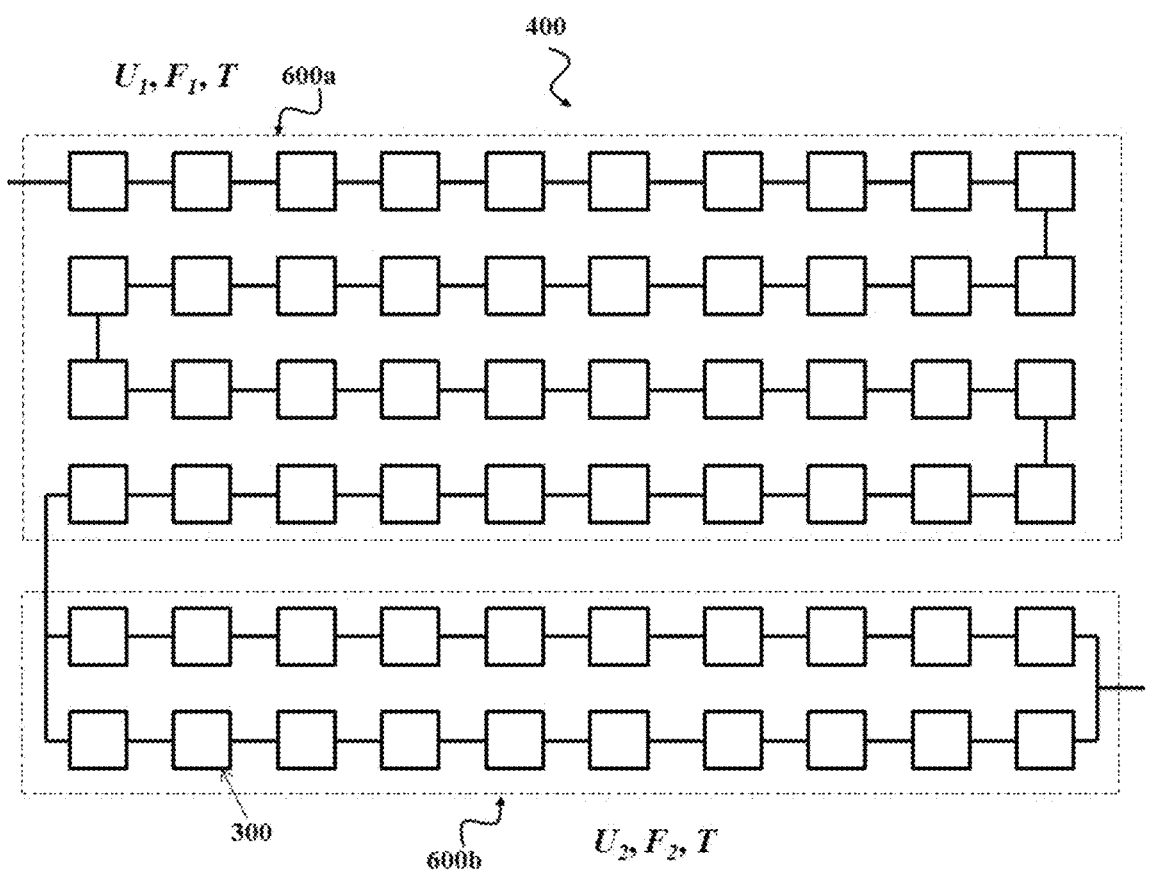
FIG. 13 is a schematic diagram of the arrangement of reaction units and layout of the array induced electric field in embodiment 8.

The extraction of yellow horn oil comprises the following steps:

Step 1: setting the reaction unit to generate a 'positive' or 'negative' induced electric field using the second way, wherein all primary coils 104 and the power supplies 101 are in parallel connection, the polarity of the excitation voltage are 'positive', and the winding of the glass spiral tubes 201 in the reactors 200 are clockwise; then a 'positive' induced electric field appeared in reaction unit 300 including with the primary coil 104 of clockwise winding, and a 'negative' induced electric field appeared in reaction unit 301 with the primary coil 104 of counterclockwise winding;

Step 2: 10 kg of 60 meshes shiny-leaved yellow horn are located into a 200 L sample container 107, taking n-hexane as an extractant, adding the extractant into the container 107, and mixing the reaction medium uniformly;

Step 3: starting the constant-temperature circulating bath 102 and the constant-temperature bath 108 at 48° C. In this embodiment, sixty reaction units are utilized, and the winding of the primary coils 104 in all sixty reaction units 300 are clockwise. Sixty 'positive' induced electric fields appear in all the reaction units (reaction unit array 400). Meanwhile, in the system, forty reaction units 300 are in series connection 600a, and twenty reaction units 300 are in parallel connection 600b, as shown in FIG. 13. Also, a disposable flowing reaction is utilized, that is the system 100b;

Step 4: starting the power supplies 101 by using sine wave, wherein the frequencies are 800 Hz and 700 Hz as well as the voltage levels are 900 V and 500 V, respectively. In the embodiment, sixty reaction units in the system are the series-connection/parallel-connection configuration. The condition parameters are set as: the excitation voltage is $U_1$=900 V and $U_2$=500 V, as well as the frequency is $F_1$=800 Hz and $F_2$=700 Hz, respectively, and the temperature T is 48° C. The $U_1$, $F_1$ and T acting on the forty reaction units 300 of 600a, whereas the $U_2$, $F_2$ and T acting on the twenty reaction units 300 of 600b are shown in FIG. 13. The actual power $P_0$ of each power supply 101 is 50 kW. And, the primary coil 104 wound on the closed nickel-steel core 103 in each reaction unit is excited via the power supply, wherein the central circumference of the closed nickel-steel core 103 is 1000 mm, and its thickness is 22 mm. The turns of the primary coils 104 in the forty reaction units 300 of 600a is 120, the impedance $Z_p$ of the primary coil 104 is detected to be 300Ω at 800 Hz by an impedance analyzer, the current $I_p$ of each primary coil 104 on each reaction unit 300 of 600a is 3 A, and the output power of the single reaction unit 300 of 600a is $P_n$=$U_P$×$I_P$=2.7 kW. The turns of the glass spiral tube 201, namely the secondary coil, in each of the forty reaction units 300 (600a) is 23, and the inner diameter of each glass spiral tube 201 is 4 mm. Thus, the total output power of this 'series' region (600a) is 108 kW ($P_0$+$P_0$+$P_0$=150 kW>$P_1$+$P_2$ . . . +$P_{39}$+$P_{40}$=108 kW) so that three power supplies can ensure all forty reaction units 300 of 600a operating smoothly. On the other hand, the turns of the primary coils 104 in the twenty reaction units 300 of 600b is 100, the impedance $Z_p$ of the primary coil 104 is detected to be 250Ω at 700 Hz by the impedance analyzer, the current $I_p$ of each primary coil 104 on each reaction unit 300 of 600b is 2 A, and the output power of a single reaction unit 300 is $P_n$=$U_P$×$I_P$=1 kW. The turns of the glass spiral tube 201, namely the secondary coil, in each of the twenty reaction units 300 (600b) is 25, and the inner diameter of each glass spiral tube 201 is 4 mm. Thus, the total output power of this 'parallel' region (600b) is 20 kW ($P_0$=50 kW>$P_1$+$P_2$ . . . $P_{19}$+$P_{20}$=20 kW) so that one power supply can ensure all twenty reaction units 300 of 600b operating smoothly. Therefore, four power supplies are configured in the system;

Step 5: starting a pump 106 for driving the feed medium disposable flowing and then passes through the system at a flow rate of 5 L/min. The total reaction time is 38 min. After the treatment, stopping the power supplies 101, the pump 106, the constant-temperature bath 108 and the constant-temperature circulating bath 102; and Step 6: discharging the reaction medium and filtering the liquid, thereby separating shiny-leaved yellow horn residues from the extractant; and performing vacuum rotary evaporation on the medium at 55° C. for recycling the n-hexane, thereby obtaining the shiny-leaved yellow horn oil with a mass of 4526 g. Compared with the control, no excitation voltage is applied on the primary coils 104, and the mass of the obtained shiny-leaved yellow horn oil is just 1093 g.

It should be noted that all the drawings in the embodiments are a simple form, which are used to aid the depiction of the embodiments conveniently and clearly in the present invention.

It should be understood that the embodiments merely illustrate technical conceptions and features of the present invention, which aims to enable persons familiar with this technology to understand and implement various uses of the present invention. However, it does not intend to limit the protection scope of the present invention. Equivalent changes or modifications made per the spiritual substance of the present invention should fall within the protection scope of the present invention.

What is claimed is:

1. An array induced electric field fluid reaction system comprising:
    a reaction unit array comprises an array of m*n reaction units connected in a network configuration, wherein the m and the n are positive integers larger than 1;
    each reaction unit further comprises
    a closed iron core with a first side and a second side,
    a primary coil wound around the first side of the closed iron core, and
    a secondary coil wound around the second side of the closed iron core, wherein the secondary coil comprises an insulation pipe for circulating feed liquid, and the insulation pipe has a sample feeding inlet and a sample discharge outlet;
    a power supply connected to the primary coil in each reaction unit providing the excitation voltage for each primary coil; and
    a feed liquid container in communication with the sample feeding inlet and the sample discharge outlet in the reaction unit array;
    wherein, in the reaction unit array, the sample feeding inlet and the sample discharge outlet of the insulation pipe of at least one reaction unit are, respectively, connected to the sample discharge outlet of the insulation pipe of at least one upstream reaction unit and the sample feeding inlet of the insulation pipe of at least one downstream reaction unit, and,
    in the reaction unit array, the sample feeding inlet and the sample discharge outlet of the insulation pipe of at least one reaction unit are, respectively, connected to the sample feeding inlet and the sample discharge outlet of the insulation pipe of at least another reaction unit,
    in the reaction unit array, two winding ends of each primary coil are, respectively, electrically connected to two electrodes of the corresponding power supply,
    wherein an excitation voltage $U_{m,n}$, a frequency $F_{m,n}$, and a temperature $T_{m,n}$ of the array induced electric field fluid reaction system can be expressed by matrixes:

$$U = \begin{bmatrix} u_{11} & u_{12} & L & u_{1n} \\ u_{21} & u_{22} & L & u_{2n} \\ u_{31} & u_{32} & L & u_{3n} \\ L & L & & L \\ u_{m1} & u_{m2} & L & u_{mn} \end{bmatrix} f = \begin{bmatrix} f_{11} & f_{12} & L & f_{1n} \\ f_{21} & f_{22} & L & f_{2n} \\ f_{31} & f_{32} & L & f_{3n} \\ L & L & & L \\ f_{m1} & f_{m2} & L & f_{mn} \end{bmatrix}$$

$$T = \begin{bmatrix} T_{11} & T_{12} & L & T_{1n} \\ T_{21} & T_{22} & L & T_{2n} \\ T_{31} & T_{32} & L & T_{3n} \\ L & L & & L \\ T_{m1} & T_{m2} & L & T_{mn} \end{bmatrix},$$

wherein $u_{ij}$ is excitation voltage of each reaction unit, $F_{ij}$ is frequency of each reaction unit, and $T_{ij}$ is temperature of each reaction unit.

2. The array induced electric field fluid reaction system of claim 1, wherein, in the reaction unit array, each primary coil is wound in a first direction, and each secondary coil is wound in a first direction or second direction, the first direction is opposite to the second direction; or in the reaction unit array, at least one primary coil is wound in a first direction, at least another primary coil is wound in a second direction, the secondary coil is wound in the first direction or the second direction.

3. The array induced electric field fluid reaction system of claim 1, wherein the power supply can yield sine waves, saw-tooth waves, triangular waves, unipolar pulses and bipolar pulses in a frequency range of 50-1300 Hz or 10-220 kHz with a voltage between 0-200 kV.

4. The array induced electric field fluid reaction system of claim 1, wherein the closed iron core is made from at least one of silicon steel, nickel steel or ferrite material.

5. The array induced electric field fluid reaction system of claim 1, wherein each reaction unit further comprises a reactor, the insulation pipe, namely the secondary coil, is arranged in the reactor, and two ends of the insulation pipe are exposed from the reactor and act as a feeding inlet and a discharge outlet respectively.

6. The array induced electric field fluid reaction system of claim 5, wherein each reaction unit further comprises a temperature-control unit for adjusting the temperature of the constant-temperature fluid, the temperature-control unit further comprises a constant-temperature jacketed layer for circulating a constant-temperature fluid, the constant-temperature jacketed layer is arranged in the reactor and covers the insulation pipe, the constant-temperature jacketed layer is further in communication with a constant-temperature fluid inlet and a constant-temperature fluid outlet, which are distributed on the reactor, the constant-temperature fluid inlet and the constant-temperature fluid outlet on the reactor are connected to a constant-temperature circulating bath.

7. The array induced electric field fluid reaction system of claim 6, wherein the constant-temperature fluid inlet and the constant-temperature fluid outlet on at least one reactor are, respectively, connected to a constant-temperature fluid outlet on at least one upstream reactor and a constant-temperature fluid inlet on at least one downstream reactor, and/or, the constant-temperature fluid inlet and the constant-temperature fluid outlet on at least one reactor are, respectively, connected to the constant-temperature fluid inlet and the constant-temperature fluid outlet on at least another reactor.

8. The array induced electric field fluid reaction system of claim 1, wherein an actual power of the power supply is $P_0 \geq P_1 + P_2 + \ldots + P_x$, wherein $P_1$ is the output power of a first reaction unit, $P_2$ is the output power of a second reaction unit, and $P_x$ is the output power of the xth reaction unit; and $P_x = U_P \times I_P = (U_P/Z_P) \times U_P$, wherein $U_P$ is the output voltage of the power supply, $Z_P$ is an impedance of a single primary coil at operating frequency, $I_P$ is a current of the single primary coil, and x is a maximum number of reaction units that can be driven by each power supply.

9. Applications of the array induced electric field fluid reaction system, according to claim 1, in agro-food processing and/or chemical reactions, wherein the agro-food processing and/or chemical reactions comprise at least one of electrocatalysis, synthesis, extraction, hydrolysis, sterilization, inactivation of enzyme and modification.

10. The array induces electric field fluid reaction system of claim 1, wherein, in the reaction unit array, each primary coil is wound in a first direction, and each secondary coil is wound in a first direction or second direction, the first direction is opposite to the second direction; or in the reaction unit array, at least one primary coil is wound in a first direction, at least another primary coil is wound in a second direction, the secondary coil is wound in the first direction or the second direction.

* * * * *